(12) United States Patent
Ribble et al.

(10) Patent No.: US 11,096,500 B2
(45) Date of Patent: Aug. 24, 2021

(54) FLOOR-SUPPORTED GRADUATED LATERAL ROTATION APPARATUS

(71) Applicant: Hill-Rom Services, Inc., Batesville, IN (US)

(72) Inventors: David L. Ribble, Batesville, IN (US); Kirsten M. Emmons, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 384 days.

(21) Appl. No.: 16/022,852

(22) Filed: Jun. 29, 2018

(65) Prior Publication Data
US 2019/0015244 A1 Jan. 17, 2019

Related U.S. Application Data

(60) Provisional application No. 62/531,987, filed on Jul. 13, 2017.

(51) Int. Cl.
*A47C 20/04* (2006.01)
*A61F 5/56* (2006.01)
(Continued)

(52) U.S. Cl.
CPC .......... *A47C 20/04* (2013.01); *A47C 19/025* (2013.01); *A47C 19/04* (2013.01); *A47C 20/041* (2013.01); *A61F 5/56* (2013.01)

(58) Field of Classification Search
CPC ......... A61F 5/56; A47C 19/00; A47C 19/005; A47C 19/02; A47C 19/021; A47C 19/024;
(Continued)

(56) References Cited

U.S. PATENT DOCUMENTS 3,775,785 A 12/1973 Mittendorf
4,754,510 A 7/1988 King
(Continued)

FOREIGN PATENT DOCUMENTS

DE 3900384 C1 * 10/1990 ........... A47C 20/048
DE 4137631 A1 5/1992
(Continued)

OTHER PUBLICATIONS

English Translation of the abstract of DE 3,900,384 to Neubauer (Year: 1990).*
(Continued)

*Primary Examiner* — Eric J Kurilla
*Assistant Examiner* — Amanda L Bailey
(74) *Attorney, Agent, or Firm* — Barnes & Thornburg LLP

(57) ABSTRACT

A lateral rotation apparatus includes a first frame, a second frame, and a third frame that are independently rotatable. The first frame, the second frame, and the third frame support a person support surface having head, torso, and leg segments. A first pair of legs is positioned below the first frame to rotate a head segment to a head tilt angle in the range of about 7 to about 30 degrees relative to a horizontal support plane. A second pair of legs is positioned below the second frame to rotate a torso segment to a torso tilt angle that is within a range of about 5 degrees to about 10 degrees less than the head tilt angle.

19 Claims, 20 Drawing Sheets

(51) Int. Cl.
   *A47C 19/04* (2006.01)
   *A47C 19/02* (2006.01)

(58) Field of Classification Search
   CPC ..... A47C 19/025; A47C 19/04; A47C 19/028;
   A61G 13/009; A61G 7/005; A61G 7/015;
   A61G 7/018; A61H 2201/0142; A47B
   2009/003
   See application file for complete search history.

(56) References Cited

U.S. PATENT DOCUMENTS

| | | |
|---|---|---|
| 4,807,313 A | 2/1989 | Ryder et al. |
| 5,092,007 A | 3/1992 | Hasty |
| 5,097,551 A | 3/1992 | Smith |
| 5,611,096 A | 3/1997 | Bartlett et al. |
| 5,640,729 A | 6/1997 | Marino |
| 5,745,937 A | 5/1998 | Weismiller et al. |
| 5,754,998 A | 5/1998 | Selton |
| 5,910,080 A | 6/1999 | Selton |
| 5,966,762 A | 10/1999 | Wu |
| 6,047,419 A | 4/2000 | Ferguson |
| 6,081,950 A | 7/2000 | Selton |
| 6,154,900 A | 12/2000 | Shaw |
| 6,163,903 A | 12/2000 | Weismiller et al. |
| D446,676 S | 8/2001 | Mayes |
| 6,370,716 B1 | 4/2002 | Wilkinson |
| 6,485,441 B2 | 11/2002 | Woodward |
| 6,536,056 B1 | 3/2003 | Vrzalik et al. |
| 6,578,219 B1 | 6/2003 | Gabel et al. |
| 6,671,907 B1 | 1/2004 | Zuberi |
| 6,681,424 B1 | 1/2004 | Bourgraf et al. |
| 6,751,817 B1 | 6/2004 | Leach |
| 6,904,631 B2 | 6/2005 | Vrzalik et al. |
| 7,007,327 B2 | 3/2006 | Ogawa et al. |
| 7,017,213 B2 | 3/2006 | Chisari |
| 7,089,615 B1 | 8/2006 | Parimuha |
| D527,937 S | 9/2006 | Aiken et al. |
| 7,346,945 B2 | 3/2008 | Phillips et al. |
| 7,418,751 B1 | 9/2008 | Bartlett et al. |
| 7,464,422 B2 | 12/2008 | Townsend |
| 7,513,003 B2 | 4/2009 | Mossbeck |
| 7,654,974 B2 | 2/2010 | Bass |
| 7,690,059 B2 | 4/2010 | Lemire et al. |
| 7,805,784 B2 | 10/2010 | Lemire et al. |
| 7,861,334 B2 | 1/2011 | Lemire et al. |
| 7,886,379 B2 | 2/2011 | Benzo et al. |
| 7,962,981 B2 | 6/2011 | Lemire et al. |
| 7,975,335 B2 | 7/2011 | O'Keefe et al. |
| 8,006,332 B2 | 8/2011 | Lemire et al. |
| 8,220,091 B2 | 7/2012 | Schultz |
| 8,261,380 B2 | 9/2012 | Ferraresi et al. |
| 8,356,602 B2 | 1/2013 | Crocetti |
| 8,393,026 B2 | 3/2013 | Dionne et al. |
| 8,413,271 B2 | 4/2013 | Blanchard et al. |
| 8,544,126 B2 | 10/2013 | Elliott et al. |
| 8,661,586 B2 | 3/2014 | Melcher et al. |
| 8,689,376 B2 | 4/2014 | Becker et al. |
| 8,695,134 B2 | 4/2014 | Schultz |
| 8,701,229 B2 | 4/2014 | Lemire et al. |
| 8,720,447 B2 | 5/2014 | North |
| 8,756,736 B1 | 6/2014 | Minson |
| 8,789,222 B2 | 7/2014 | Blanchard et al. |
| 8,832,887 B2 | 9/2014 | Mossbeck |
| 8,844,076 B2 | 9/2014 | Becker et al. |
| 8,870,764 B2 | 10/2014 | Rubin |
| 9,038,217 B2 | 5/2015 | Elliot et al. |
| 9,126,571 B2 | 9/2015 | Lemire et al. |
| 2006/0179580 A1 | 8/2006 | Robertson et al. |
| 2007/0163051 A1 | 7/2007 | Straub |
| 2008/0040861 A1* | 2/2008 | Ootayopas ........... A61G 7/0573 5/715 |
| 2008/0109965 A1 | 5/2008 | Mossbeck |
| 2008/0148487 A1 | 6/2008 | Lord et al. |
| 2009/0089930 A1* | 4/2009 | Benzo ................ A61G 7/015 5/613 |
| 2009/0250070 A1 | 10/2009 | Pfeifer |
| 2011/0231996 A1 | 9/2011 | Lemire et al. |
| 2012/0138067 A1 | 6/2012 | Rawls-Meehan |
| 2012/0222214 A1 | 9/2012 | Lachenbruch et al. |
| 2013/0198965 A1 | 8/2013 | Melcher et al. |
| 2013/0245395 A1 | 9/2013 | Bidarian Moniri |
| 2014/0059768 A1 | 3/2014 | Lemire et al. |
| 2014/0088373 A1 | 3/2014 | Phillips et al. |
| 2014/0173829 A1 | 6/2014 | Melcher et al. |
| 2014/0180036 A1 | 6/2014 | Bukkapatnam et al. |
| 2014/0245539 A1 | 9/2014 | Ooba |
| 2014/0259417 A1 | 9/2014 | Nunn et al. |
| 2014/0259418 A1 | 9/2014 | Nunn et al. |
| 2014/0259419 A1 | 9/2014 | Stusynski et al. |
| 2014/0259433 A1 | 9/2014 | Nunn et al. |
| 2014/0259434 A1 | 9/2014 | Nunn et al. |
| 2014/0266733 A1 | 9/2014 | Hayes et al. |
| 2014/0277611 A1 | 9/2014 | Nunn et al. |
| 2014/0283302 A1 | 9/2014 | Horstmann |
| 2014/0366274 A1 | 12/2014 | Melcher et al. |
| 2015/0000035 A1 | 1/2015 | Becker et al. |
| 2017/0277822 A1 | 9/2017 | Clark et al. |

FOREIGN PATENT DOCUMENTS

| | | | |
|---|---|---|---|
| EP | 262771 | A1 | 4/1988 |
| EP | 2140847 | A2 | 1/2010 |
| EP | 2175822 | A1 | 4/2010 |
| EP | 2494946 | A2 | 9/2012 |
| JP | 2011143237 | A | 7/2011 |
| KR | 20110083167 | A | 7/2011 |
| WO | 2010048310 | A1 | 4/2010 |
| WO | 2013031504 | A1 | 3/2013 |
| WO | 2013116676 | A1 | 8/2013 |
| WO | 2013166003 | A1 | 11/2013 |
| WO | 2013177338 | A2 | 11/2013 |
| WO | 2014069713 | A1 | 5/2014 |
| WO | 2014149392 | A1 | 9/2014 |
| WO | 2014151707 | A1 | 9/2014 |
| WO | 2014152891 | A1 | 9/2014 |

OTHER PUBLICATIONS

Adesanya, Adebola O., et al., *Perioperative Management of Obstructive Sleep Apnea*, Chest/138/6, Dec. 2010 (10 pages).

Ankichetty, Saravanan and Frances Chung, *Considerations for Patients with Obstructive Sleep Apnea Undergoing Ambulatory Surgery*, Current Opinion in Anesthesiology 2011, 24:605-611 (7 pages).

Arnold, Donald H., et al., *Estimation of Airway Obstruction Using Oximeter Plethysmograph Waveform Data*, Respiratory Research 2005, 6:65 (8 pages).

American Society of Anesthesiologists, Inc., *Practice Guidelines for the Perioperative Management of Patients with Obstructive Sleep Apnea*, Anesthesiology 2006, V. 104, 1081-93, No. 5, May 2006, (13 pages).

Benumof, Jonathan L., *Obstructive Sleep Apnea in the Adult Obese Patient: Implications for Airway Management*, Journal of Clinical Anesthesia 13:144-156, 2001 (13 pages).

Berend, Keith R., et al., *Prevalence and Management of Obstructive Sleep Apnea in Patients Undergoing Total Joint Arthroplasty*, The Journal of Arthroplasty vol. 25 No. 6 Suppl. 1 2010 (4 pages).

Berger, G., et al., *Progression of Snoring and Obstructive Sleep Apnoea: The Role of Increasing Weight and Time*, European Respiratory Journal, vol. 33, No. 2, 2009 (8 pages).

Bianchi, Matt T., *Screening for Obstructive Sleep Apnea: Bayes Weighs in*, The Open Sleep Hournal, 2009, 2, 56-59 (4 pages).

Bignold, James J., et al., *Accurate Position Monitoring and Improved Supine-Dependent Obstructive Sleep Apnea with a New Position Recording and Supine Avoidance Device*, Journal of Clinical Sleep Medicine, vol. 7, No. 4, 2001 (8 pages).

Bloom, Harrison G., et al., *Evidence-Based Recommendations for the Assessment and Management of Sleep Disorders in Older Persons*, J Am Geriatr Soc 57:761-789, 2009 (30 pages).

(56) References Cited

OTHER PUBLICATIONS

Bolden, Norman, et al., *Avoiding Adverse Outcomes in Patients with Obstructive Sleep Apnea (OSA): Development and Implementation of a Perioperative OSA Protocol*, Journal of Clinical Anesthesia (2009) 21, 286-293 (8 pages).

Bourne, Richard S., et al., *Clinical Review: Sleep Measurement in Critical Care Patients: Research and Clinical Implications*, Critical Care 2007, 11:226 (17 pages).

Brown, Carlos VR and George C. Velmahos, *The Consequences of Obesity on Trauma, Emergency Surgery, and Surgical Critical Care*, World Journal of Emergency Surgery 2006, 1:27 (5 pages).

Bush, Haydn, *Screening for Sleep Apnea*, American Hospital Association Health Forum, Hospital & Health Networks, hhn@omeda.com, 2013 (2 pages).

Camilo, Millene R., et al., *Supine Sleep and Positional Sleep Apnea After Acute Ischemic Stroke and Intracerebral Hemorrhage*, Clinics 2012; 67(12); 1357-1360 (4 pages).

Carr, Gordon E., et al., *Acute Cardiopulmonary Failure From Sleep-Disordered Breathing*, Chest 2012; 141(3); 798-808 (11 pages).

Casey, Kenneth R. and Michael J. Lefor, *Management of the Hospitalized Patient with Sleep Disordered Breathing*, Current Opinion in Pulmonary Medicine 2002, 8:511-515 (5 pages).

Chia, P., et al., *The Association of Pre-Operative STOP-BANG Scores with Postoperative Critical Care Admission*, Anaesthesia 2013, 68, 950-952 (3 pages).

Choi, Jae-Kap, et al., *Effect of Jaw and Head Position on Airway Resistance in Obstructive Sleep Apnea*, Sleep and Breathing, vol. 4, No. 4, 163-168, 2000 (8 pages).

Choi, Ji Ho, et al., *Efficacy Study of a Vest-Type Device for Positional Therapy in Position Dependent Snorers*, Sleep and Biological Rhythms 2009; 7; 181-187 (7 pages).

Chung, Sharon A., et al., *Systemic Review of Obstructive Sleep Apnea and Its Implications for Anesthesiologists*, Ambulatory Anesthesiology, vol. 107, No. 5, Nov. 2008, 1543-1563 (21 pages).

Chung, F., et al., *High STOP-Band Score Indicates a High Probability of Obstructive Sleep Apnoea*, British Journal of Anaesthesia 108 (5): 768-75 (2012), (8 pages).

Chung, Frances and Babak Mokhlesi, *Postoperative Complications Associates with Obstructive Sleep Apnea: Time to Wake Up!*, Anesthesia & Analgesia, Feb. 2014, vol. 118, No. 2, 251-253 (3 pages).

Chung, Frances et al., *Preoperative Identification of Sleep Apnea Risk in Elective Surgical Patient6s, Using the Berlin Questionnaire*, Journal of Clinical Anesthesia (2007) 19, 130-134 (5 pages).

Chung, Frances and Hisham Elsaid, *Screening for Obstructive Sleep Apnea Before Surgery: Why is it Important?*, Current Opinion in Anaesthesiology 2009, 22:405-411 (7 pages).

Chung, Frances, et al., *Validation of the Berlin Questionnaire and American Society of Anesthesiologists Checklist as Screening Tools for Obstructive Sleep Apnea in Surgical Patients*, Anesthesiology, vol. 108, No. 5, May 2008, 822-830 (9 pages).

Curry, J. Paul and Lawrence A. Lynn, *Threshold Monitoring, Alarm Fatigue, and the Patterns of Unexpected Hospital Death*, The Official Journal of the Anesthesia Patient Safety Foundation, Fall 2011 (8 pages).

D'Apuzzo, Michele R. and James A. Browne, *Obstructive Sleep Apnea as a Risk Factor for Postoperative Complications After Revision Joint Arthroplasty*, The Journal of Arthroplasty, vol. 27, No. 8, Suppl. 1 (2012), 95-98 (4 pages).

der Herder, Cindy, et al., *Risks of General Anaesthesia in People with Obstructive Sleep Apnoea*, British Medical Journal, vol. 329, Oct. 23, 2004, 955-959 (5 pages).

Dolezal, Donna, et al., *Implementing Preoperative Screening of Undiagnosed Obstructive Sleep Apnea*, Journal of PeriAnesthesia Nursing, vol. 26, No. 5 Oct. 2011, 338-342 (5 pages).

Ead, Heather, *Meeting the Challenge of Obstructive Sleep Apnea: Developing a Protocol that Guides Perianesthesia Patient Care*, Journal of PeriAnesthesia Nursing, vol. 24, No. 2 Apr. 2009, 103-113 (11 pages).

Farney, Robert J., et al., *The STOP-Bang Equivalent Model and Prediction of Severity of Obstructive Sleep Apnea: Relation to Polysomnographic Measurements of the Apnea/Hypopnea Index*, Journal of Clinical Sleep Medicine, vol. 7, No. 5, 2011, 459-467 (9 pages).

Finkel, Kevin J., et al., *Prevalence of Undiagnosed Obstructive Sleep Apnea Among Adult Surgical Patients in an Academic Medical Center*, Sleep Medicine 10 (2009) 753-758 (6 pages).

Finucane, Thomas E., *Evidence-Based Recommendations for the Assessment and Management of Sleep Disorders in Older Persons*, JAGS, Nov. 2009, vol. 57, No. 11, 2173-2174 (3 pages).

Fletcher, Eugene C., *"Near Miss" Death in Obstructive Sleep Apnea: A Critical Care Syndrome*, Critical Care Medicine, vol. 19, No. 9, Sep. 1991, 1158-1164 (7 pages).

Galhotra, Sanjay, *Mature Rapid Response System and Potentially Avoidable Cardiopulmonary Arrests in Hospital*, Qual. Saf. Health Care 2007, 16:260-265 (6 pages).

Gammon, Brian T. and Karen F. Ricker, *An Evidence-Based Checklist for the Postoperative Management of Obstructive Sleep Apnea*, Journal of PeriAnesthesia Nursing, vol. 27, No. 5 Oct. 2012, 316-322 (7 pages).

Gay, Peter C., *Sleep and Sleep-Disordered Breathing in the Hospitalized Patient*, Respiratory Care, Sep. 2010, vol. 55, No. 9, 1240-1254 (15 pages).

Gay, Peter C., *The Value of Assessing Risk of Obstructive Sleep Apnea in Surgical Patients: It Only Takes One*, Journal of Clinical Sleep Medicine, vol. 6, No. 5, 2010, 473-474 (2 pages).

Global Industry Analysts, Inc., *GIA Market Report: Sleep Apnea Diagnostic and Therapeutic Devices, A Global Strategic Business Report*, MCP-3307, Oct. 2010, www.StrategyR.com, (321 pages).

Gibson, G. J., *Obstructive Sleep Apnoea Syndrome: Underestimated and Undertreated*, British Medical Bulletin 2004; 72: 49-64 (16 pages).

Gupta, Rakesh M., et al., *Postoperative Complications in Patients With Obstructive Sleep Apnea Syndrome Undergoing Hip or Knee Replacement: A Case-Control Study*, May Clin Proc. 2001; 76:897-905 (9 pages).

Guralnick, Amy S., et al., *CPAP Adherence in Patients with Newly Diagnosed Obstructive Sleep Apnea Prior to Elective Surgery*, Journal of Clinical Sleep Medicine, vol. 8, No. 5, 2012, 501-506 (6 pages).

Heinzer, Raphael C., et al., *Positional Therapy for Obstructive Sleep Apnea: An Objective Measurement of Patients' Usage and Efficacy at Home*, Sleep Medicine 13 (2012) 425-428 (4 pages).

Hoque, Enamul, et al., *Monitoring Body Positions and Movements During Sleep Using WISPs*, Wireless Health '10, Oct. 5-7, 2010 (10 pages).

Isono, Shiroh, et al., *Lateral Position Decreases Collapsibility of the Passive Pharynx in Patients with Obstructive Sleep Apnea*, Anesthesiology, vol. 97, No. 4, Oct. 2002, 780-785 (6 pages).

Itasaka, Yoshiaki and Kazuo Ishikawa, *The Influence of Sleep Position and Obesity on Sleep Apnea*, Psychiatry and Clinical Neurosciences (2000), 54, 340-341 (3 pages).

Jensen, Candice, et al., *Postoperative CPAP and BiPAP Use Can be Safely Omitted after Laparoscopic Roux-en-Y Gastric Bypass*, Surgery for Obesity and Related Diseases 4 (2008) 512-514 (3 pages).

Joho, Shuji, et al., *Impact of Sleeping Position on Central Sleep Apnea/Cheyne-Stokes Respiration in Patients with Heart Failure*, Sleep Medicine 11 (2010) 143-148 (6 pages).

Jokie, Ruzica, et al., *Positional Treatment vs. Continuous Positive Airway Pressure in Patients with Positional Obstructive Sleep Apnea Syndrome*, Chest/115/3/Mar. 1999, 771-781 (11 pages).

Joosten, S.A., et al., *Obstructive Sleep Apnea Phenotypic Trait Changes from Supine to Lateral Position*, Am J Respir Crit Care Med 189; 2014; A3909 (1 page).

Joshi, Girish P., et al., *Society for Ambulatory Anesthesia Consensus Statement on Preoperative Selection of Adult Patients with Obstructive Sleep Apnea Scheduled for Ambulatory Surgery*, Anesthesia & Analgesia, Nov. 2012, vol. 115, No. 5, 1060-1068 (9 pages).

Keenan, Sean P., et al., *Clinical Practice Guidelines for the Use of Noninvasive Positive-Pressure Ventilation and Noninvasive Continuous Positive Airway Pressure in the Acute Care Setting*, Canadian Medical Association Journal, Feb. 22, 2011, 183(3) (21 pages).

(56) References Cited

OTHER PUBLICATIONS

Khayat, Rami, et al., In-Hospital Resting for Sleep-Disordered Breathing in Hospitalized Patients with Decompensated Heart Failure: Report of Prevalence and Patient Characteristics, *Journal of Cardiac Failure*, vol. 15, No. 9 (2009) (739-746).
Kim, Eun Joong, *The Prevalence and Characteristics of Positional Sleep Apnea in Korea*, Korean J Otorhinolaryngol-Head Neck Surg. 2009:52:407-12 (6 pages).
Kulkarni, Gaurav V., et al., *Obstructive Sleep Apnea in General Surgery Patients: Is it More Common than we Think?*, The American Journal of Surgery (2014) 207, 436-440 (5 pages).
Lakdawala, Linda, *Creating a Safer Perioperative Environment With an Obstructive Sleep Apnea Screening Tool*, Journal of PeriAnesthesia Nursing, vol. 26, No. 1 Feb. 2001, 15-24 (10 pages).
Lee, Chul Hee, et al., *Changes in Site of Obstruction in Obstructive Sleep Apnea Patients According to Sleep Position: A DISE Study*, Laryngoscope 00: Month 2014 (7 pages).
Lee, Jung Bok, et al., *Determining Optimal Sleep Position in Patients with Positional Sleep-Disordered Breathing Using Response Surface Analysis*, J. Sleep Res. (2009) 18, 26-35 (10 pages).
Lockhart, Ellen M., et al. *Obstructive Sleep Apnea Screening and Postoperative Mortality in a Large Surgical Cohort*, Sleep Medicine 14 (2013) 407-415 (9 pages).
Lynn, Lawrence A. and J. Paul Curry, *Patterns of Unexpected In-Hospital Deaths: A Root Cause Analysis*, Patient Safety in Surgery 2011, 5:3 (25 pages).
Mador, M. Jeffrey, et al., *Are the Adverse Effects of Body Position in Patients with Obstructive Sleep Apnea Dependent on Sleep Stage?*, Sleep Breath (2010) 14:13-17 (7 pages).
Mador, M. Jeffrey, et al., *Prevalence of Positional Sleep Apnea in Patients Undergoing Polysomnography*, Chest 2005; 128:2130-2137 (8 pages).
Marcus, Howard, *Obesity and Postoperative Surgical Risk*, The Doctors Company, Third Quarter 2010, 1-8 (8 pages).
Martin-Du Pan, Rémy, et al., *The Role of Body Position and Gravity in the Symptoms and Treatment of Various Medical Diseases*, Swiss Med. Wkly. 2004: 134:543-551 (10 pages).
Memtsoudis, Stavros G., et al., *A Rude Awakening—The Perioperative Sleep Apnea Epidemic*, N Engl. J. Med. 368:25, 2352-2353 (Jun. 20, 2013) (2 pages).
Menon, Akshay and Manoj Kumar, *Influence of Body Position on Severity of Obstructive Sleep Apnea: A Systematic Review*, Otolaryngology, vol. 2013, Article ID 670381 (2013) (8 pages).
Mininni, Nicolette C., et al., *Pulse Oximetry: An Essential Tool for the Busy Med-Surg Nurse*, American Nurse Today, Nov./Dec. 2009, 31-33 (3 pages).
Mokhlesi, Babak, *Empiric Postoperative Autotitrating Positive Airway Pressure Therapy / Generating Evidence in the Perioperative Care of Patients at Risk for Obstructive Sleep Apnea*, Chest 144/1 (Jul. 2013) 5-7 (3 pages).
Mull, Yvonne and Marshall Bedder, *Obstructive Sleep Apnea Syndrome in Ambulatory Surgical Patients*, AORN Journal, vol. 76, No. 3, 458-462 (Sep. 2002) (5 pages).
Nader, Nizar Z., et al., *Newly Identified Obstructive Sleep Apnea in Hospitalized Patients: Analysis of an Evaluation and Treatment Strategy*, Journal of Sleep Medicine, vol. 2, No. 4, 2006, 431-437 (7 Pages).
Pevernagie, Dirk A., et al., *Effects of Body Position on the Upper Airway of Patients with Obstructive Sleep Apnea*, Am J Respir Crit Care Med, vol. 152, 179-185, 1995 (7 pages).
Qureshi, Asher and Robert D. Ballard, *Obstructive Sleep Apnea*, J Allergy Clin Immunol, vol. 112, No. 4, 643-651 (2003) (9 pages).
Richard, Wietske, et al., *The Role of Sleep Position in Obstructive Sleep Apnea Syndrome*, Eur Arch Otorhinolaryngol (2006) 263:946-950 (5 pages).
Rocke, Daniel, et al., *Effectiveness of a Postoperative Disposition Protocol for Sleep Apnea Surgery*, American Journal of Otolaryngology—Head and Neck Medicine and Surgery 34 (2013) 273-277 (5 pages).

Gabbott, D.A., *The Effect of Single-Handed Cricoid Pressure on Neck Movement After Applying Manual In-Line Stabilisation*, Anaesthesia, 1997, 52, 586-602 (17 pages).
Ross, Jacqueline, *Obstructive Sleep Apnea: Knowledge to Improve Patient Outcomes*, Journal of PeriAnesthesia Nursing, vol. 23, No. 4 Aug. 2008, 273-275 (3 pages).
Setaro, Jill, *Obstructive Sleep Apnea: A Standard of Care That Works*, Journal of PeriAnesthesia Nursing, vol. 27, No. 5 Oct. 2012, 323-328 (6 pages).
Sheldon, Alison, et al., *Nursing Assessment of Obstructive Sleep Apnea in Hospitalised Adults: A Review of Risk Factors and Screening Tools*, Contemporary Nurse, vol. 34, Issue 1, Dec. 2009/Jan. 2010, 19-33 (16 pages).
Skinner, Margot A., et al., *Efficacy of the 'Tennis Ball Technique' Versus nCPAP in the Management of Position-Dependent Obstructive Sleep Apnoea Syndrome*, Respirolgy (2008) 13, 708-715 (8 pages).
Stearns, Joshua D. and Tracey L. Stierer, *Peri-Operative Identification of Patients at Risk for Obstructive Sleep Apnea*, Seminars in Anesthesia, Perioperative Medicine and Pain (2007) 26, 73-82 (10 pages).
van Kesteren, Ellen R., et al., *Quantitative Effects of Trunk and Head Position on the Apnea Hypopnea Index in Obstructive Sleep Apnea*, Sleep, vol. 34, No. 8 (2011), 1075-1081 (7 pages).
Veasey, Sigrid C., et al., *Medical Therapy for Obstructive Sleep Apnea: A Review by the Medical Therapy for Obstructive Sleep Apnea Task Force of the Standards of Practice Committee of the American Academy of Sleep Medicine*, Sleep, vol. 29, No. 8 (2006), 1036-1044 (9 pages).
Wolfson, Alexander, et al., *Postoperative Analgesia for Patients with Obstructive Sleep Apnea Syndrome*, Seminars in Anesthesia, Perioperative Medicine and Pain (2007), 26, 103-109 (7 pages).
Yantis, Mary Ann, *Decreasing Surgical Risks for Patients with Obstructive Sleep Apnea*, AORN Journal, vol. 68, No. 1 (Jul. 1998), 50-55 (6 pages).
Ravesloot, M.J.L., and N. de Vries, *Reliable Calculation of the Efficacy of Non-Surgical Treatment of Obstructive Sleep Apnea Revisted*, Sleep, vol. 34, No. 1 (2011), 105-110 (6 pages).
Moon, Il Joon, et al., *Sleep Magnetic Resonance Imagine as a New Diagnostic Method in Obstructive Sleep Apnea Syndrome*, Laryngoscope 120: Dec. 2010, 2546-2554 (9 pages).
Nepomnayshy, Dmitry, et al., *Sleep Apnea: Is Routine Preoperative Screening Necessary?*, OBES Surg (2013) 23:287-192 (5 pages).
Press Release: *World's Leading Health Media Promotes Disinformation on Best Sleeping Positions* (Sep. 22, 2010), Sleeping Positions Research Summary (24 Studies), http://www.normalbreathing.com/I-6-best-sleep-positions.php (14 pages).
Oksenberg, Arie, et al., *Association of Body Position with Severity of Apneic Events in Patients with Severe Nonpositional Obstructive Sleep Apnea*, Chest 2000; 118; 1018-1024 (9 pages).
Oksenberg, Arie, *The Avoidance of the Supine Posture during Sleep for Patients with Supine-related Sleep Apnea*, BSM Protocols for Adherence and Treatment of Intrinsic Sleep Disorders, Chapter 23, 223-236 (14 pages).
Oksenberg, Arie and Donald Silverberg, *The Effect of Body Posture on Sleep-Related Breathing Disorders: Facts and Therapeutic Implications*, Sleep Medicine Reviews, vol. 2, No. 3, 139-162 (1998) (25 pages).
Oksenberg, Arie, et al., *Positional Therapy for Obstructive Sleep Apnea Patients: A 6-Month Follow-Up Study*, Laryngoscope 116, Nov. 2006, 1995-2000 (6 pages).
Oksenberg, Arie, et al., *REM-Related Obstructive Sleep Apnea: The Effect of Body Position*, Journal of Clinical Sleep Medicine, vol. 6, No. 4 (2010), 343-348 (6 pages).
Ozeke, Ozcan, et al., *Influence of the Right- Versus Left-Sided Sleeping Position on the Apnea-Hypopnea Index in Patients with Sleep Apnea*, Sleep Breath, published online Jun. 16, 2011 (5 pages).
Ozeke, Ozcan, et al., *Sleep Apnea, Heart Failure, and Sleep Position*, Sleep Breath, published online Nov. 9, 2011 (4 pages).
Permut, Irene, et al., *Comparison of Positional Therapy to CPAP in Patients with Positional Obstructive Sleep Apnea*, Journal of Clinical Sleep Medicine, vol. 6, No. 3 (2010), 238-243 (6 pages).

(56) References Cited

OTHER PUBLICATIONS

Author Unknown, *Positioning of Surgical Patients With Sleep Apnea*, ClinicalTrials.gov, http://clinicaltrials.gov/ct2/show/NCT02123238?term=apnea+and+position&rank=3 (2014) (5 pages).
Author Unknown, *Obstructive Sleep Apnea May Block the Path to a Positive Postoperative Outcome*, 2007 Pennsylvania Patient Safety Authority, reprinted from the PA-PSRS Patient Safety Advisory, vol. 4, No. 3 (Sep. 2007) (9 pages).
Proczko, Monika, et al., *STOP-Bang and the Effect on Patient Outcome and Length of Hospital Stay when Patients are not Using Continuous Positive Airway Pressure*, J Anesth, published online May 29, 2014 (7 pages).
Ramachandran, Satya Krishna, et al., *Derivation and Validation of a Simple Perioperative Sleep Apnea Prediction Score*, Society for Ambulatory Anesthesiology, vol. 110, No. 4 (Apr. 2010), 1007-1015 (9 pages).
Ravesloot, M.J.L. and N. de Vries, *Calculation of Surgical and Non-Surgical Efficacy for OSA / Reliable Calculation of the Efficacy of Non-Surgical and Surgical Treatment of Obstructive Sleep Apnea Revisted*, vol. 34, Issue 01 (2001) 105-110 (2 pages).
Ravesloot, M.J.L., et al., *The Undervalued Potential of Positional Therapy in Position-Dependent Snoring and Obstructive Sleep Apnea—A Review of the Literature*, Sleep Breath, published online Mar. 24, 2012 (11 pages).
Ravesloot, Madeline J.L., et al., *Treatment Adherence Should be Taken into Account when Reporting Treatment Outcomes in Obstructive Sleep Apnea*, Sleep Medicine, vol. 124, Issue 1 (Jan. 2014) 344-345 (3 pages).
Richardson, Annette and Anne Killen, *How Long do Patients Spend Weaning from CPAP in Critical Care?*, Intensive and Critical Care Nursing (2006) 22, 206-213 (8 pages).
Rosenberg, Russell and Paul Doghramji, *Optimal Treatment of Obstructive Sleep Apnea and Excessive Sleepiness*, Springer Healthcare Communication, published online Apr. 3, 2009, 295-312 (18 pages).
Rosenthal, Leon, *Got CPAP? Use it in the Hospital!*, Sleep Breath, published online Nov. 25, 2011 (4 pages).
Safiruddin, Faiza, et al., *Analysis of the Influence of Head Rotation During Drug-Induced Sleep Endoscopy in Obstructive Sleep Apnea*, Laryngoscope 124: Sep. 2014, 2195-2199 (5 pages).
Seet, Edwin and Frances Chung, *Obstructive Sleep Apnea: Preoperative Assessment*, Anesthesiology Clin 28 (2010) 199-215 (17 pages).
Seet, Edwin, et al., *Perioperative Clinical Pathways to Manage Sleep-Disordered Breathing*, Sleep Med Clin 8 (2013) 105-120 (16 pages).
Sforza, Emilia, et al., *A 3-Year Longitudinal Study of Sleep Disordered Breathing in the Elderly*, European Respiratory Journal, vol. 40, No. 3 (2012) 665-672 (8 pages).
Sforza, E., et al., *Natural Evolution of Sleep Apnoea Syndrome: A Five Year Longitudinal Study*, European Respiratory Journal, 1994, 7, 1765-1770 (6 pages).
Shafazand, Shirin, *Perioperative Management of Obstructive Sleep Apnea: Ready for Prime Time?*, Cleveland Clinic Journal of Medicine, vol. 76, Supp. 4, Nov. 2009 (6 pages).
Siddiqui, Fouzia, et al. *Half of Patients with Obstructive Sleep Apnea have a Higher NREM AHI than REM AHI*, Sleep Medicine 7 (2006) 281-285 (5 pages).
Singh, M., et al., *Proportion of Surgical Patients with Undiagnosed Obstructive Sleep Apnoea*, British Journal of Anaesthesia 110 (4); 629-636 (2013) (8 pages).
Skinner, Margot A., et al., *Elevated Posture for the Management of Obstructive Sleep Apnea*, Sleep and Breathing, vol. 8, No. 4 (2004) 193-200 (10 pages).
Author Unknown, *There's More than One Way to Improve Nightime Breathing*, European Sleep Works, http://www.sleepworks.com/resource/medical-needs/sleep-apnea (2014) (3 pages).
Park, Steven V., *Sleep Apnea CPAP Compliance Craziness*, Doctor Steven Y_ Park, MD New York, NY Integrative Solutions for Obstructive Sleep Apnea, Upper Airway Resistance Syndrome, and Snoring (Nov. 10, 2009) (7 pages).
Monk, Timothy H., et al., *Measuring Sleep Habits Without Using a Diary: The Sleep Timing Questionnaire*, Sleep, vol. 26, No. 2 (2003) 208-212 (5 pages).
Sorscher, Adam J. and Evan M. Caruso, *Frequency of Provision of CPAP in the Inpatient Setting: An Observational Study*, Sleep Breath, published online Nov. 23, 2011 (6 pages).
Spurr, Kathy F., et al., Prevalence of Unspecified Sleep Apnea and the use of Continuous Positive Airway Pressure in Hospitalized Patients, *2004 National Hospital Discharge Survey*, Sleep Breath (2008) 12:229-234 (8 pages).
Srijithesh PR, et al., *Positional Therapy for Obstructive Sleep Apnoea (Protocol)*, The Cochrane Library 2014, Issue 2 (11 pages).
Sundar, Eswar, et al., *Perioperative Screening for the Management of Patients with Obstructive Sleep Apnea*, JCOM, vol. 18, No. 9, Sep. 2011, 399-411 (13 pages).
Szollosi, Irene, et al., *Lateral Sleeping Position Reduces Severity of Central Sleep Apnea/Cheyne-Stokes Respiration*, Sleep, vol. 29, No. 8 (2006), 1045-1051 (7 pages).
Author Unknown, *A Promising Concept of Combination Therapy for Positional Obstructive Sleep Apnea*, Springer Link, http://link.springer.com/article/10.1007/s11325-014-1068-8, Oct. 2014 (4 pages).
Author Unknown, *Upper Airway Collapse During Drug Induced Sleep Endoscopy: Head Rotation in Supine Position Compared with Lateral Head and Truck Position*, Springer Link, http://link.springer.com/article/10.1007/s00405-014-3215-z, Aug. 2014 (4 pages).
Vasu, Tajender S., et al., *Obstructive Sleep Apnea Syndrome and Postoperative Complications*, Arch Otolaryngol Head Neck Surg, vol. 136, No. 10, Oct. 2010 (5 pages).
Matthews, Dan, *Mattresses—A Futile Weapon in the Fight Against Sleep Apnea*, http://www.danmatthewsdds.com/mattresses-%E2%80%93-futile-weapon-fight-sleep-apnea/ (2014) (1 page).
Marks, Steve, *Hospital Care of Patients with Sleep Apnea*, Areté Sleep Health, last modified on May 16, 2013 (63 pages).
Carlisle, Heather, *The Case for Capnography in Patients Receiving Opioids*, American Nurse Today, vol. 9, No. 9 (Sep. 2014) 22-27 (69 pages).
Gold, Jenny, *The Sleep Apnea Business Is Booming, and Insurers Aren't Happy*, NPR_Apnesvsinsurere.mht, (Jan. 16, 2012) (3 page).
Author unknown, Sleep right, Sleep tight, Natural sleep before medicines, *Sleep Diary*, www.nps.org.au/sleep, last modified Jul. 7, 2010 (4 pages).
Quan, S. F., *Evolution of OSA*, Thorax 1998; 53:532 (4 pages).
Maurer, J. T., et al., *Treatment of Obstructive Sleep Apnea with a New Vest Preventing the Supine Position*, Thieme-Connect (2003) (1 page).
Schreuder, K.E., *The Effect of Cervical Positioning on Benign Snoring by Means of a Custom-Fitted Pillow*, Centre for Sleep and Wake Disorders Kempenhaeghe, 5591 VE HEEZE, the Netherlands, last modified Dec. 1, 2011 (4 pages).
Chung, Frances, *Semi-up Right Position Study*, Clinical Trials.gov, last updated May 28, 2014 (5 pages).
Author Unknown, *National Sleep Foundation Sleep Diary*, National Sleep Foundation, last modified Apr. 18, 2003 (2 pages).
Takaoka, Shanon, CPAP Adherence, Is it too much "pressure"?, Feb. 7, 2007 (41 pages).
Seren, Suaf, *The Effect of Pure Prone Positioning Therapy for the Patients With Mild to Moderate Obstructive Sleep Apnea*, ClinicalTrials.gov, last updated Jun. 7, 2011 (4 pages).
Jackman, Shawn M. and Bruce Hubbert, *Riding the Wireless Wave (without wiping out)*, HIMSS12 Annual Conference & Exhibition, last modified Feb. 20, 2012 (133 pages).
de Vries, Nico and Madeline Ravesloot, *Apnea Calculator*, http://apneacalculator.com (2014) (2 pages).
Oexman, Robert, *Can a Mattress Really Impact Your Sleep?*, Huffpost Healthy Living, Posted Oct. 14, 2012, 10:00 a.m. (8 pages).
Palmer, Laura and Suzanne R. Morrison, *Obesity and Obstructive Sleep Apnea / Is there a limit for ambulatory surgery?*, OR Nurse Journal, Sep. 2014 (9 pages).

(56) References Cited

OTHER PUBLICATIONS

Oksenberg, Arie, *Are We Missing a Simple Treatment for Most Adults Sleep Apnea Patients? The Avoidance of the Supine Sleep Position*, ResearchGate.net, Aug. 12, 2014 (2 pages).

Author Unknown, *Obstructive Sleep Apnea (OSA), Care of Adult Patients*, St. Anthony Central Hospital Clinical Standards, Jul. 8, 2009 (9 pages).

Gross, Jeffrey B., *Practice Guidelines for the Perioperative Management of Patients with Obstructive Sleep Apnea: An Updated Report by the American Society of Anesthesiologists Task Force on Perioperative Management of Patients with Obstructive Sleep Apnea*, U.S. Department of Health & Human Services, updated on May 9, 2014 (13 pages).

O'Connor, Anahad, *Treating Sleep Apnea Without the Mask*, NYTimes.com, Apr. 9, 2012 (7 pages).

Stradling, J. R. and R. J. O. Davies, *Sleep 1: Obstructive Sleep Apnea/Hypopnoea Syndrome: Definitions, Epidemiology, and Natural History*, Thorax 2004;59:73-78 (6 pages).

Pyke, Josh, et al, *Continuous Pulse Oximetry Monitoring in the Inpatient Population*, Patient Safety & Quality Healthcare, May/Jun. 2009 (5 pages).

EP Search Report for Application No. EP 13 79 3571, dated Sep. 8, 2015 (9 pages).

Service Manual—"TotalCare® Bed System" from Hill-Rom, Product No. P1900, MAN112 Rev 7, by Hill-Rom Services, Inc. (2007) (1105 pages).

User Manual—"TotalCare® Bed System" from Hill-Rom, Product No. P1900, USR042 REV11, by Hill-Rom Services, Inc. (2007) (112 pages).

SleepEducation—Blog, "Positional therapy harness helps reduce sleep apnea for some," www.sleepeducation.com, posted Friday, Jun. 18, 2010 (7 pages).

SPANAmerica: PressureGuard® TurnSelect®, www.archive.org/web/20090201172625/http://spanamerica.com/turn_select.php; Aug. 18, 2014 (2 pages).

PCT Search Report and Written Opinion for PCT/US2014/18033, completed Aug. 18, 2014.

PCT Search Report for PCT/US2013/042313, completed Dec. 6, 2013.

EP Search Report for Application No. 15180086.9-1651, dated Dec. 22, 2015, 7 pages.

Japanese Office Action for Japanese Patent Application No. 2017-073542 dated Feb. 7, 2018 and its English translation; 11 pages total.

Japanese Patent Application Publication No. JP 2011-143237A dated Jul. 28, 2011 and its machine-generated English translation; 34 pages total.

PCT Patent Application Publication No. WO 2013/031504 A1 published on Mar. 7, 2018 and the English translation of the Abstract only; 63 pages total.

\* cited by examiner

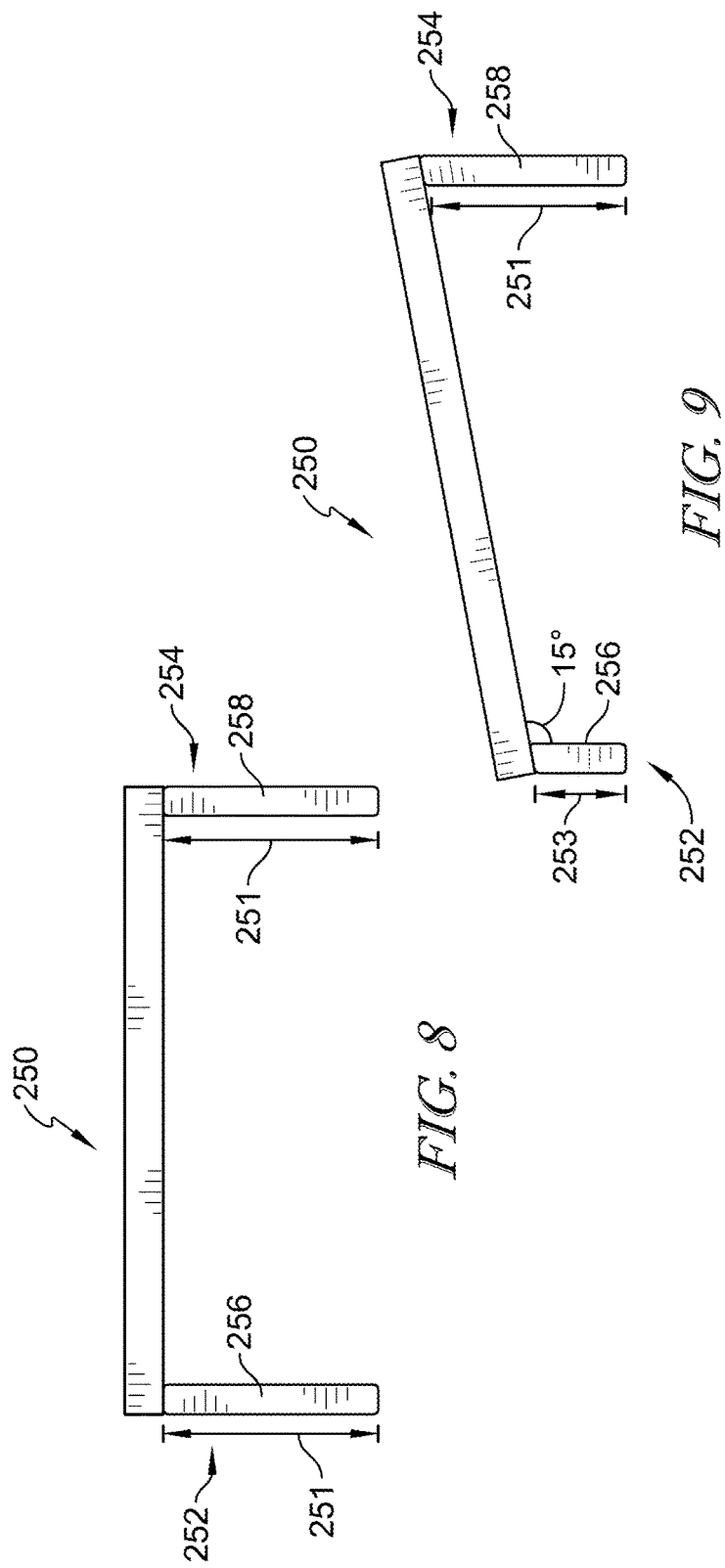

FLOOR-SUPPORTED GRADUATED LATERAL ROTATION APPARATUS

CROSS-REFERENCE TO RELATED APPLICATIONS

This application claims priority to U.S. Provisional Patent Application Ser. No. 62/531,987, filed Jul. 13, 2017 and titled "FLOOR-SUPPORTED GRADUATED LATERAL ROTATION APPARATUS," which is herein incorporated by reference in its entirety.

BACKGROUND

The subject matter disclosed herein relates generally to adverse event mitigation devices, systems, and methods and, more particularly, but not exclusively, to devices, systems, and methods for the prevention and treatment of sleep apnea. These devices, systems, and methods may include an active intervention, a passive intervention, of a continuous intervention. The embodiments described herein may also be effective in reducing snoring.

While various adverse event mitigation devices, systems, and methods have been developed, there is still room for improvement. Thus, a need persists for further contributions in this area of technology.

SUMMARY

The present disclosure includes one or more of the features recited in the appended claims and/or the following features which, alone or in any combination, may comprise patentable subject matter.

In one aspect, a lateral rotation apparatus includes a person support surface having head, torso and leg segments each having an independently rotatable person support plane. A first pair of adjustable legs is positioned below the head segment. The first pair of adjustable legs including a first leg and a second leg. At least one of the first leg and the second leg of the first pair of adjustable legs being adjustable such that a height of the first leg is greater than a height of the second leg to rotate the head segment to a head tilt angle approximately at a centerline of the head segment in the range of about 7 to about 30 degrees relative to a horizontal support plane. A second pair of adjustable legs is positioned below the torso segment. The second pair of adjustable legs includes a first leg and a second leg. At least one of the first leg and the second leg of the second pair of adjustable legs being adjustable such that a height of the first leg is greater than a height of the second leg to rotate the torso segment to a torso tilt angle approximately at a centerline of the torso segment that is within a range of about 5 degrees to about 10 degrees less than the head tilt angle. The first pair of adjustable legs and the second pair of adjustable legs provide a graduated lateral rotation of the person support surface.

In some embodiments, the first leg of the first pair of adjustable legs positions a first side of the head segment at a height greater than a second side of the head segment. In some embodiments, the first leg of the second pair of adjustable legs positions a first side of the torso segment at a height greater than a second side of the torso segment.

In some embodiments, at least one of the first leg or the second leg of the first pair of adjustable legs includes a telescoping leg. In some embodiments, at least one of the first leg or the second leg of the second pair of adjustable legs includes a telescoping leg.

In some embodiments, a height of at least one of the first leg or the second leg of the first pair of adjustable legs is adjusted with an actuator. In some embodiments, the actuator includes an electromechanical device configured to drive a height adjustment of the at least one of the first leg or the second leg of the first pair of adjustable legs. In some embodiments, a height of at least one of the first leg or the second leg of the second pair of adjustable legs is adjusted with an actuator. In some embodiments, the actuator includes an electromechanical device configured to drive a height adjustment of the at least one of the first leg or the second leg of the second pair of adjustable legs.

In some embodiments, the head segment is coupled to the torso segment via a linkage assembly that enables rotation of the head segment with respect to the torso segment. In some embodiments, the torso segment is coupled to the leg segment via a linkage assembly that enables rotation of the torso segment with respect to the leg segment.

In some embodiments, the torso segment is rotated to a torso tilt angle approximately at a centerline of the torso segment in the range of about zero to about 25 degrees.

In some embodiments, the head segment is rotated to a head tilt angle approximately at a centerline of the head segment in the range of about 10 to about 15 degrees. In such an embodiment, the torso segment is rotated to a torso tilt angle approximately at a centerline of the torso segment in the range of about 5 to about 10 degrees.

In some embodiments, a third pair of legs is positioned under the leg segment and is operable to rotate the leg segment to a leg tilt angle approximately at a centerline of the leg segment in the range of about 0 to about 5 degrees.

In some embodiments, the person support surface includes a support material having a density. The head tilt angle is a function of the density of the support material. In some embodiments, the torso tilt angle is a function of the density of the support material.

In another aspect, a lateral rotation apparatus includes a first frame and a second frame that are independently rotatable. The first frame and the second frame support a person support surface. At least one leg is positioned below at least one of the first frame and the second frame. The at least one leg is adjustable to rotate the first frame approximately at a centerline of the first frame to a first tilt angle in the range of about 7 to about 30 degrees relative to a horizontal support plane, and to rotate the second frame to a second tilt angle approximately at a centerline of the second frame that is within a range of about 5 degrees to about 10 degrees less than the first tilt angle. At least one linkage assembly couples the at least one leg to at least one of the first frame and the second frame. The linkage assembly rotates at least one of the first frame and the second frame with respect to the at least one leg. The first frame and the second frame provide a graduated lateral rotation of the person support surface.

In some embodiments, the at least one leg includes a first leg and a second leg that are operable to adjust such that the first leg has a height greater than the second leg. In some embodiments, the at least one leg positions a first side of the first frame at a height greater than a second side of the first frame. In some embodiments, the at least one leg positions a first side of the second frame at a height greater than a second side of the second frame.

In some embodiments, the at least one leg includes a telescoping leg. In some embodiments, a height of the at least one of leg is adjusted with an actuator. In some embodiments, the actuator includes an electromechanical device.

In some embodiments, the linkage assembly enables rotation of the first frame with respect to the second frame. In some embodiments, the linkage assembly enables rotation of the second frame with respect to a third frame.

In some embodiments, the second frame is rotated to a second tilt angle approximately at a centerline of the second frame in the range of about zero to about 25 degrees.

In some embodiments, the first frame is rotated to a first tilt angle approximately at a centerline of the first frame in the range of about 10 to about 15 degrees. In such an embodiment, the second frame is rotated to a second tilt angle approximately at a centerline of the second frame in the range of about 5 to about 10 degrees. In some embodiments, the at least one leg is adjustable to rotate a third frame to a third tilt angle approximately at a centerline of the third frame in the range of about 0 to about 5 degrees.

In some embodiments, the first frame includes a plurality of slats. In some embodiments, the second frame includes a plurality of slats.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 8 is an elevation view of a frame of a lateral rotation apparatus in accordance with an embodiment and having legs positioned in a first configuration;

FIG. 9 is an elevation view of the frame of FIG. 8 and having the legs positioned in a second configuration;

FIG. 10 is an elevation view of the frame of FIG. 8 and having the legs positioned in a third configuration;

DETAILED DESCRIPTION

Figure 1:
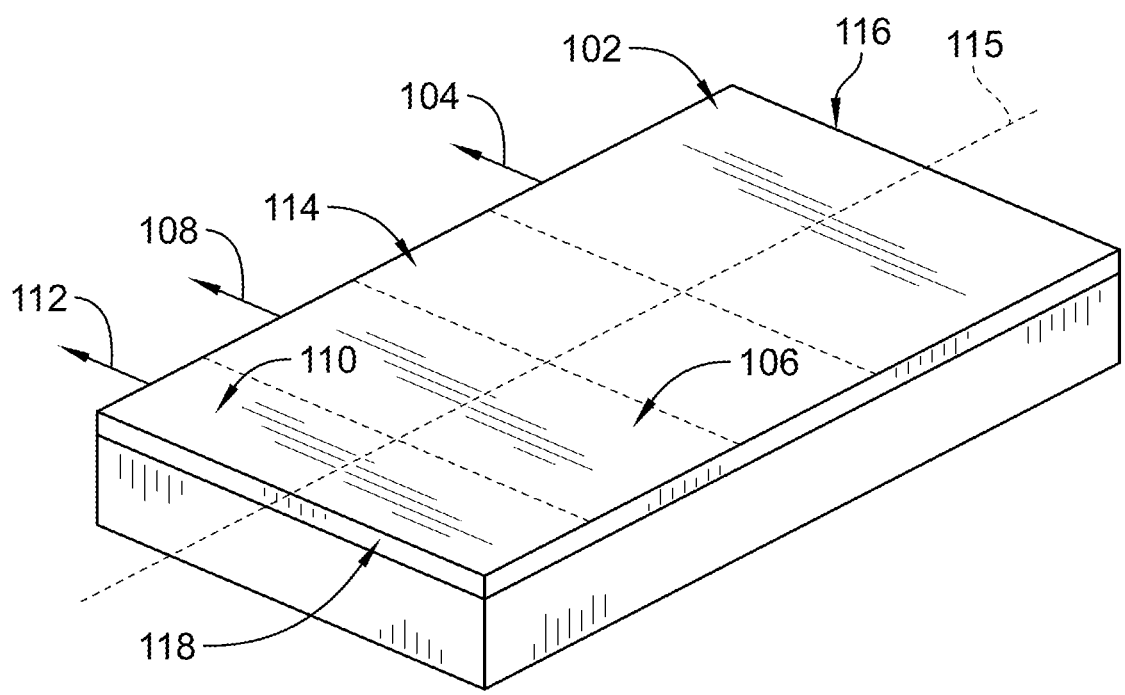
FIG. 1 is a perspective view of a patient support surface illustrated as a bed.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

The embodiments described herein relate to devices, systems and methods to reduce the occurrence and/or duration of or prevent sleep apnea events and/or snoring. The embodiments demonstrate efficacy in preventing mild to moderate obstructive sleep apnea, with improved tolerability relative to current therapy (i.e., CPAP).

The described devices, systems and methods are not limited to the specific embodiments described herein. In addition, components of each device, system and/or steps of each method may be practiced independent and separate from other components and method steps, respectively, described herein. Each component and method also can be used in combination with other systems and methods.

Referring to FIG. 1, a support system 100 includes a support surface having one or more support sections that are angled to form a lateral support plane that prevents or restricts the user from sleeping in a supine position, and, more specifically, reduces a time duration that the user sleeps with his/her upper respiratory tract oriented vertically or at an undesirable lateral rotational angle with respect to a vertical plane substantially perpendicular to a horizontal plane of the support surface. In certain embodiments, the lateral rotational angle of the user's head with respect to the vertical plane is at least 30 degrees and, more specifically, at least 45 degrees. In an alternative embodiment, the lateral rotational angle of the user's head with respect to the vertical plane may be less than 30 degrees. In one embodiment, the support sections provide multiple support planes for supporting the user's body.

Figure 2:
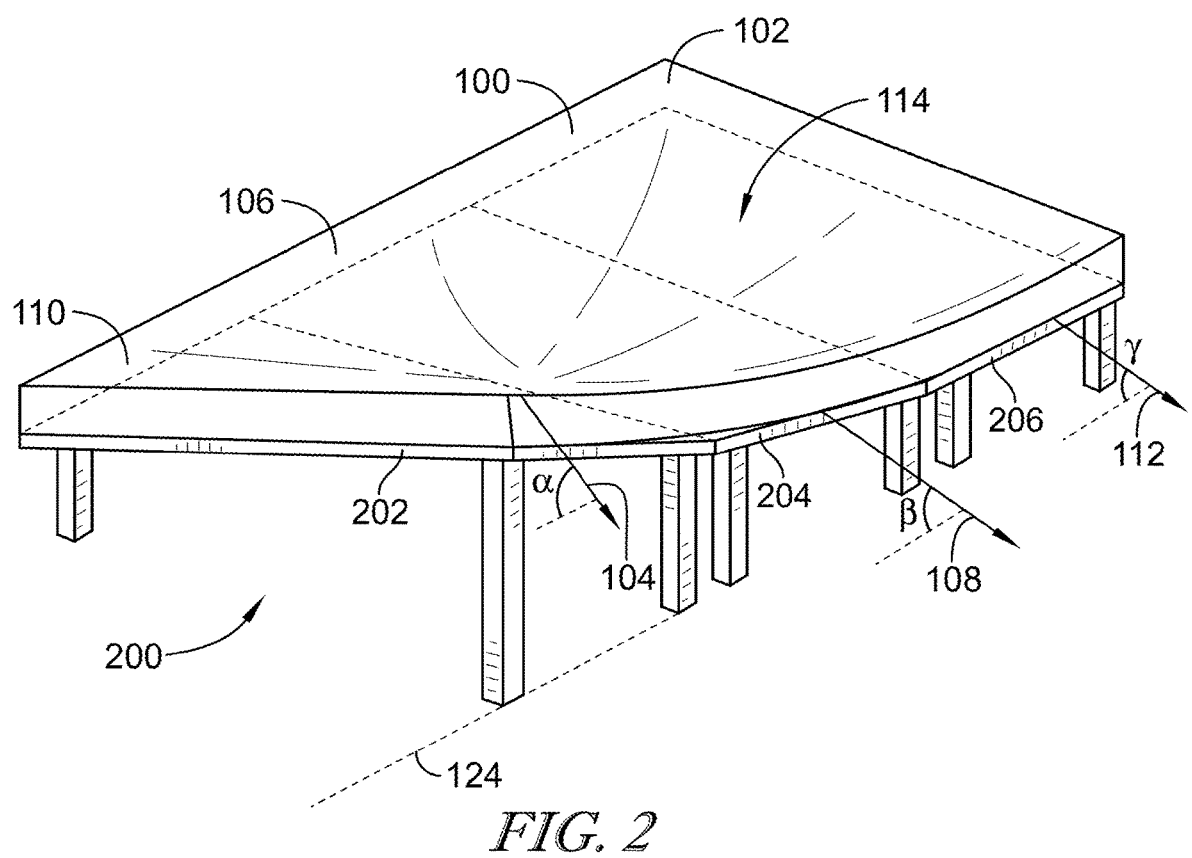
FIG. 2 is a plan view of a lateral rotation apparatus in accordance with an embodiment and having a plurality of frames supported by a plurality of legs.
Figure 3:
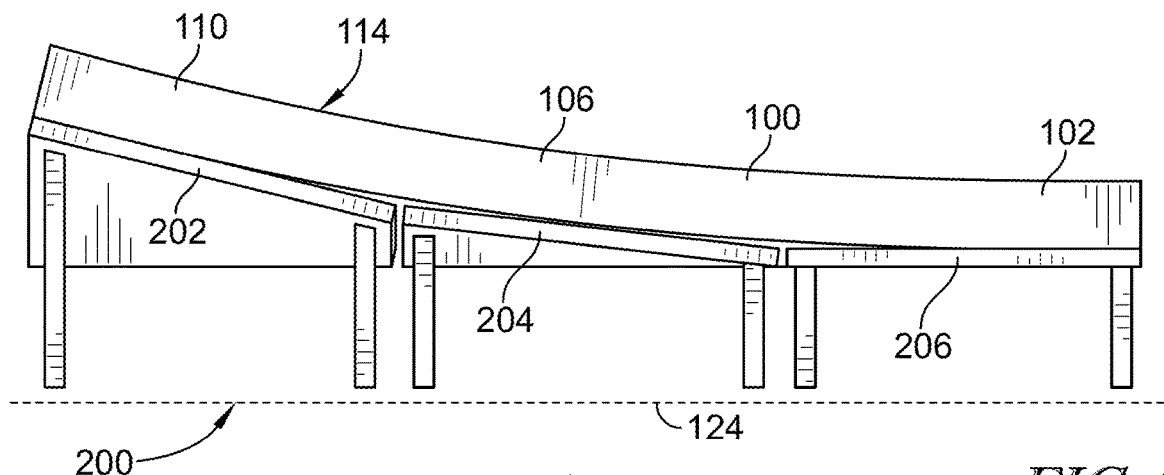
FIG. 3 is a perspective view of a lateral rotation apparatus in accordance with an embodiment and positioned between the patient support apparatus and a horizontal support plane illustrated as a floor.

In one embodiment as shown in FIG. 1-3, a support system 100 suitable for supporting a user, such as a person, for example, includes plurality of support sections, namely a first or leg support section 102 forming a first support plane 104, a second or torso support section 106 forming a second support plane 108, and a third or head support section 110 forming a third support plane 112 that collectively define a multi-plane, sleep surface 114 that may be progressively angled along a longitudinal axis 115 of support system 100, from a first or bottom edge 116 of sleep surface 114 to an opposing second or top edge 118 of sleep surface 114, resulting in relatively greater rotation of the upper respiratory tract of the user (as necessary for efficacy in preventing obstructive apnea) and relatively lesser rotation in the lower body of the user (resulting in greater comfort and perceived stability by avoiding rotation of a majority of the user's body mass).

Unlike conventional positional therapies for the prevention of obstructive sleep apnea, which attempt to manipulate the user's sleep position and/or orientation using rotation of one plane, in certain embodiments the system described herein uses multiple support planes formed by one or more support sections to laterally rotate the user. For example, in one embodiment, two support sections provide two separate support planes, with a first support plane defined by the first support section configured to support the torso and the legs of the user, and a second support plane defined by the second support section configured to support the neck and the head of the user.

In an alternative embodiment, three support sections provide three separate support planes, with a first support plane defined by the first support section configured to support the legs of the user, a second support plane defined by the second support section configured to support the torso of the user, and a third support plane defined by the third support section configured to support the head of the user.

In a further alternative embodiment, more than three support sections, for example, numerous independent support sections having a length in a longitudinal direction of sleep surface 114 of 2-18 inches or, more specifically, 4-12 inches, or, even more specifically, 6 inches, provide a corresponding number of separate support planes. Each support section can be laterally rotated independently of other support sections to collectively form sleep surface 114. In a particular embodiment, the numerous support sections can be combined to form separate support sections, for example, creating a first support section having a length of 18 inches in the longitudinal direction at the foot of the support surface, an adjacent second support section having a length of 12 inches in the longitudinal direction, and a third support section adjacent the second support section having a length in the longitudinal direction of 6 inches. In these embodiments, the support sections forming the support planes can be rotated as necessary or desired to achieve an optimal configuration that is clinically effective (i.e., prevents apnea) and demonstrates acceptable tolerance (i.e., allows the user to sleep comfortably). In an alternative embodiment, a continuously sloped sleep surface is formed by a plurality of support sections without step increases in lateral rotational angle; this is illustrated as a sleep surface with an infinite number of support sections.

In the embodiments described herein, the length in the longitudinal direction of each support section and defined support plane (and the resulting location of transitions between support planes) is designed to achieve clinical efficacy and tolerability. Therefore, a specific length can be defined in a number of configurations, including without limitations: (a) generic plane dimensions (e.g., based on average body geometry, a length of a torso section of the user defined so that when an average user's head is supported by a head support section, a transition between the torso support section and the leg support section occurs below the user's S3 vertebrae); (b) customized plane dimensions (e.g., a torso support plane has a suitable length in the longitudinal direction appropriate to the user's leg length, torso length, and/or a distance from the user's shoulder to his/her inseam); or (c) dynamic plane dimensions (e.g., transitions selected on dynamic surface appropriate to user, selection being either user-selected, care-giver defined, or automatically calculated).

Referring to FIGS. 2 and 3, a lateral rotation apparatus 200 is provided in the form of a frame positioned beneath support system 100 and secured on a horizontal support plane 124, for example a floor to provide a gradual lateral rotation of the support system 100. In the illustrative embodiment, the lateral rotation apparatus 200 includes a first adjustable frame 202, a second adjustable frame 204, and a third adjustable frame 206. The frames 202, 204, 206 are illustrated as individual separate frames that are not connected. In one embodiment, the frames 202, 204, 206 may be joined by a linkage assembly or the like that enables each frame 202, 204, 206 to be individually adjusted. Additionally or alternatively, the frames 202, 204, 206 may be secured together, for example at a base of each frame 202, 204, 206 such that each frame 202, 204, 206 is independently adjustable. The frames 202, 204, 206 may be formed from metal, plastic, or any other material suitable for supporting the support system 100.

The first frame 202 is positioned below the support section 110. The first frame 202 is operable to rotate the support section 110 to position the support section 110 at a head tilt angle relative to the horizontal support plane 124. For example, the first frame 202 may rotate the support section 110 to a head tilt angle approximately at a centerline of the support section 110 in the range of about 7 to about 30 degrees relative to a horizontal support plane. The second frame 204 is positioned below the support section 106. The second frame 204 is operable to rotate the support section 106 to a torso tilt angle relative to the horizontal support plane 124. For example, the second frame 204 may rotate the support section 106 to a torso tilt angle approximately at a centerline of the support section 106 that is within a range of about 5 degrees to about 10 degrees less than the head tilt angle. The third frame 206 is positioned below the support section 102. The third frame 206 is operable to rotate the support section 102 to a leg tilt angle relative to the horizontal support plane 124. For example, the third frame 206 may rotate the support section 102 to a leg tilt angle approximately at a centerline of the support section 102 in the range of about 0 to about 5 degrees.

In one embodiment, the support system 100 is a mattress, wherein each of the support sections 102, 106, 110 are coupled via linkage assemblies that enable support sections 102, 106, 110 to move relative to one another. For example, a first linkage assembly enables support section 102 to move relative to support section 106, and a second linkage assembly enables support section 110 to move relative to support section 106. The mattress may be formed from any conventional material, i.e. foam, down, cotton, air cushions, etc. or any suitable material utilized in a healthcare setting.

In certain embodiments, each support section defining the corresponding support surface is independently rotatable about an axis extending parallel with a longitudinal axis of the support system. The independent rotation of each support section allows the caregiver or the user ability to focus on progressively increasing an angle of rotation in one or more support sections having support planes positioned to support the torso of the user, and the neck and/or the head of the user. In certain embodiments, a rotational angle at which the one or more support planes defined by the support sections configured to support the neck and/or the head of the user is positioned is greater that a rotational angle of the one or more support planes defined by the support sections configured to support the torso of the user, which is greater than a rotational angle at which the one or more support planes defined by the support sections configured to support the legs of the user is positioned.

In a particular embodiment, the support plane defined by the support section configured to support the legs and the torso of the user is positioned at a rotational angle of approximately 10° with respect to the horizontal support plane, while the support plane defined by the support section configured to support the head of the user is positioned at a rotational angle of approximately 20° with respect to the horizontal support plane. In an alternative embodiment, a first support plane defined by the support section configured to support the legs of the user is positioned at a rotational angle of approximately 10° with respect to the horizontal support plane, a second support plane defined by a second support section configured to support the torso of the user is positioned at a rotational angle of approximately 15° with respect to the horizontal support plane, and a third support plane defined by the third support section configured to support the head of the user is positioned at a rotational angle of approximately 20° with respect to the horizontal support plane. In alternative embodiments, the support planes can be positioned at any suitable rotational angle including any suitable lateral rotational angle and/or any suitable longitudinal rotational angle.

In a particular embodiment, first support section 102 defines support plane 104 positioned at a lateral rotational angle α of approximately 20° to approximately 30° approximately at a centerline of the support section 102, or more specifically, approximately 20° to approximately 25°, or, even more specifically, approximately 25° with respect to the horizontal support plane 124. Second support section 106 defines support plane 108 positioned at a lateral rotational angle β of approximately 10° to approximately 20° approximately at a centerline of the support section 106, or more specifically, approximately 10° to approximately 15°, or, even more specifically, approximately 15°, with respect to the horizontal support plane 124. Third support section 110 defines support surface 112 positioned at a lateral rotational angle γ of approximately 5° to approximately 15° approximately at a centerline of the support section 110, or more specifically, approximately 10°, with respect to the horizontal support plane 124. Other lateral rotational angles and step increases in lateral rotational angles between each support section may also be used to achieve a progressive lateral rotational angle. It should be noted that the measured rotation of the corresponding support section 102, 106, 110 is measured approximately at a centerline of the support section 102, 106, 110. A remainder of the support section 102, 106, 110 may have a different slope due to a weight of the support system 100, e.g. the mattress, a density of the support system 100, and/or a weight of an individual on the support surface. That is, the tilt angle within a particular support section 102, 106, 110 may vary throughout the support system 100. Generally, the lateral rotation apparatus 200 slopes the support system 100 such that gradual lateral rotation is achieved between the support sections 102, 106, and 110.

Each of first support section 102, second support section 106, and third support section 110 has a respective height in a direction perpendicular to longitudinal axis 115 of support system 100. In one embodiment, first support section 102 has a maximum height from the horizontal support plane 124 to support plane 116 in a direction perpendicular to longitudinal axis 115 of 14 to 18 inches approximately at a centerline of the support section 102, or more specifically, 16 to 17 inches; second support section 106 has a maximum height from the horizontal support plane 124 to support plane 108 in a direction perpendicular to longitudinal axis 115 of 8 to 12 inches approximately at a centerline of the support section 106, or more specifically, 9 to 10 inches; and third support section 110 has a maximum height from the horizontal support plane 124 to support plane 112 in a direction perpendicular to longitudinal axis 115 of 4 to 8 inches, or more specifically, 6 to 7 inches approximately at a centerline of the support section 110. As a result, the support sections can be designed with desired heights and defining support planes positioned at desired rotational angles such that support surface 100 provides a composite longitudinal plane angle (e.g., reverse Trendelenburg angle), to facilitate the prevention and/or treatment of sleep apnea as well as to improve tolerability.

In one embodiment, each of support sections 102, 106, 110 are rotatable about longitudinal axis 115 to provide sleep surface 114 having a right side slope or, alternatively, a left side slope to allow the user to sleep on his/her right side or left side, respectively. In certain embodiments, support sections 102, 106, 110 are formed of more than one material, for example, two or more materials, such as two foam materials, having different densities, with the less dense material covering the denser material.

In this embodiment, support system 100 allows the user to sleep on either his/her right side or left side, based on the user's sleeping preference. This sleeping preference may not be static. For example, if the user has an injury, an ache, or a desire to change his/her sleeping preference, the orientation of sleep surface 114 can be changed at any time to accommodate the user's sleeping preference. The orientation can be changed from day to day or during the night. Moreover, from a manufacturing standpoint, a versatile support system 100 prevents having to manufacture and distribute a sleep surface 114 having a right side slope and a separate sleep surface 114 having a left side slope, which would increase production and distribution costs. Finally, a potential purchaser would not have to commit to a sleep side before purchasing the product, which might be a deterrent to purchasing the product.

As described herein, sleep surface 114 is customizable to anthropometric dimensions of the individual user to facilitate support surface performance that optimizes or matches the design intent—the body position of the user will prevent or limit undesirable sleep apnea episodes and provide improved comfort. As illustrated in FIGS. 2 and 3, the support sections 102, 106, 110 are not sloped evenly, e.g. the support sections 102, 106, 110 do not slope in a straight line. Rather the support sections 102, 106, 110 slope at different angles when sloping from head to foot or side to side.

Figure 4:
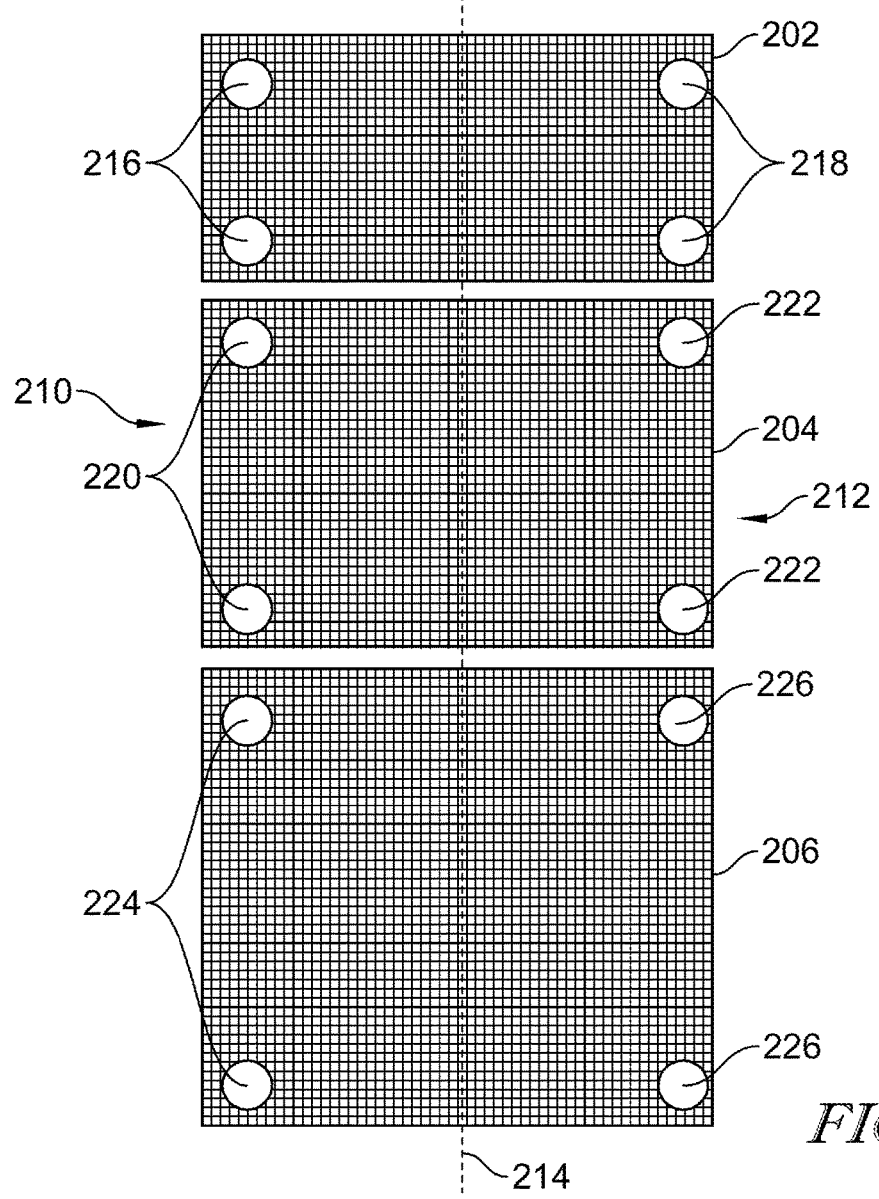
FIG. 4 is a top view of the lateral rotation apparatus positioned between the patient support apparatus and the horizontal support plane.

Referring to FIG. 4, the lateral rotation apparatus 200 includes a first side 210 and a second side 212 separated by a longitudinal axis 214. The frame 202 includes first side of legs 216 and second side of legs 218. The first side legs 216 are positioned on the first side 210 of the frame 202. The second side legs 218 are positioned on the second side 212 of the frame 202. In some embodiments, the first side legs 216 and/or the second side legs 218 are adjustable so that the first side legs 216 and the second side legs 218 have a different height. The frame 204 includes first side of legs 220 and second side of legs 222. The first side legs 220 are positioned on the first side 210 of the frame 204. The second side legs 222 are positioned on the second side 212 of the frame 204. In some embodiments, the first side legs 220 and/or the second side legs 222 are adjustable so that the first side legs 220 and the second side legs 222 have a different height. The frame 206 includes first side of legs 224 and second side of legs 226. The first side legs 224 are positioned on the first side 210 of the frame 206. The second side legs 226 are positioned on the second side 212 of the frame 206.

Figure 7:
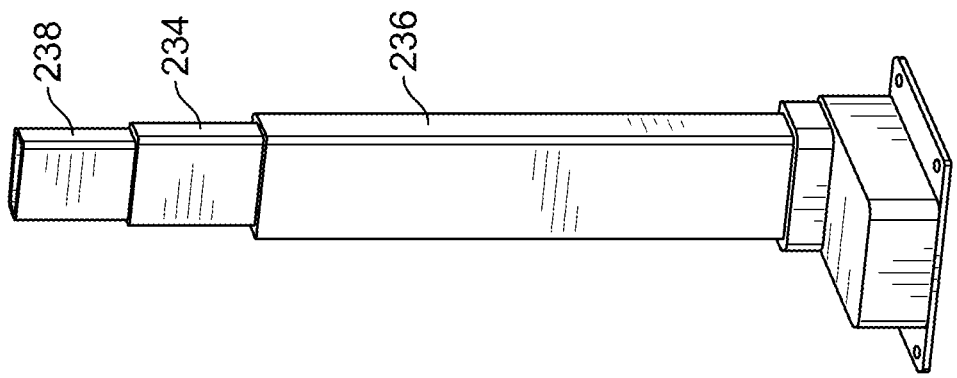
FIG. 7 is a perspective view of yet another adjustable leg in accordance with an embodiment.
Figure 6:
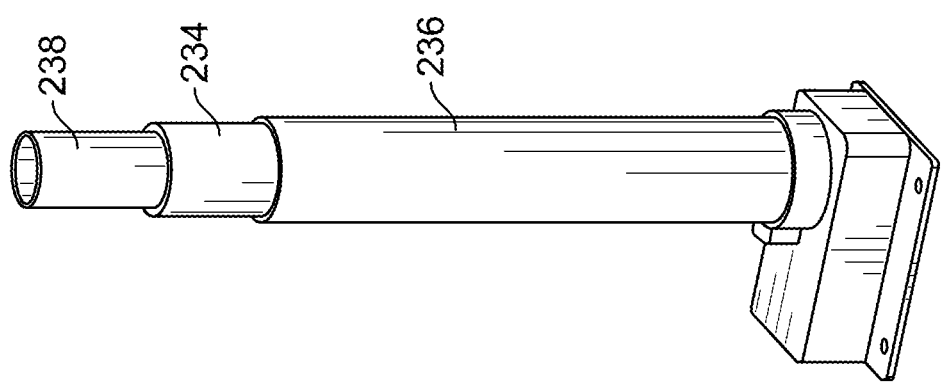
FIG. 6 is is a perspective view of another adjustable leg in accordance with an embodiment.
Figure 5:
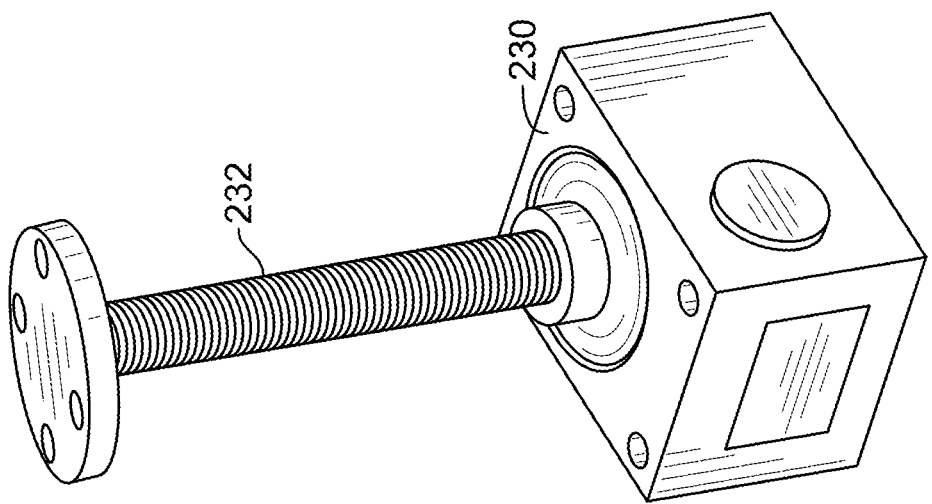
FIG. 5 is a perspective view of an adjustable leg in accordance with an embodiment.

In some embodiments, the first side legs 224 and/or the second side legs 226 are adjustable so that the first side legs 224 and the second side legs 226 have a different height. For example, the legs 224 and/or 226 may include an actuator 230 that drives a threaded shaft 232, as illustrated in FIG. 5. In another embodiment, the legs 224 and/or 226 may be telescoping, as illustrated in FIGS. 6 and 7, wherein an upper post 234 moves upward and downward through a lower post 236. In some embodiments, the upper post 234 is locked into a position with respect to the lower post 236 by a tab of the lower post 236 securing within an aperture of the upper post 234. In another embodiment, the upper post 234 may be hydraulically actuated and secured in position within the lower post 236. In the embodiment illustrated in FIG. 6 the posts 234, 236 may be round or, as illustrated in FIG. 7, the posts 234, 236 may be squared. In other embodiments, the posts 234, 236 may have any suitable shape. It should be noted that the embodiments, of FIGS. 6 and 7 also include a third post 238 that telescopes within the upper post 234 in the same manner that the upper post 234 telescopes within the lower post 236. In one embodiment, the legs 224, 226 may have any number of telescoping posts.

Referring to FIGS. 8-10, an exemplary frame 250 that may be any one of frame 202, 204, or 206. The frame 250 includes a first side 252 and a second side 254. A first leg 256 is positioned on the first side 252. The first leg 256 may be any one of first leg 216, 220, or 224, respectively. A second leg 258 is positioned on the second side 254. The second leg 258 may be any one of second leg 218, 222, or 226, respectively. As illustrated in FIG. 8, the first leg 256 and the second leg 258 may have the same height 251, such that the frame 250 is parallel to the floor (i.e. horizontal support plane 124). In one exemplary non-limiting embodiment, each leg 256, 258 may have a height 251 of 10 inches. As illustrated in FIG. 9, the first leg 256 may be adjusted so that the first leg 256 is shorter than the second leg 258. As such, the frame 250 is positioned at an angle with respect to the horizontal support plane 124. In the exemplary non-limiting embodiment, the first leg 256 is shortened to a height 253, for example 4 inches, while the second leg 258 is kept at the height 251, for example 10 inches. As such, the frame 250 is angled approximately 15° with respect to the horizontal support plane 124. In another exemplary non-limiting embodiment illustrated in FIG. 10, the first leg 256 is lowered to a height 255, for example 6 inches, and the second leg 258 is raised to a height 257, for example 12 inches, thereby achieving the same 15° angle between the frame 250 and the horizontal support plane 124.

It should be appreciated that the first leg 256 and the second frame 258 may be adjusted to achieve various angles. For example, each of frame 202, 204, and 206 may be adjusted to different angles to achieve the various head tilt angles, torso tilt angles, and leg tilt angles described above.

Figure 11:
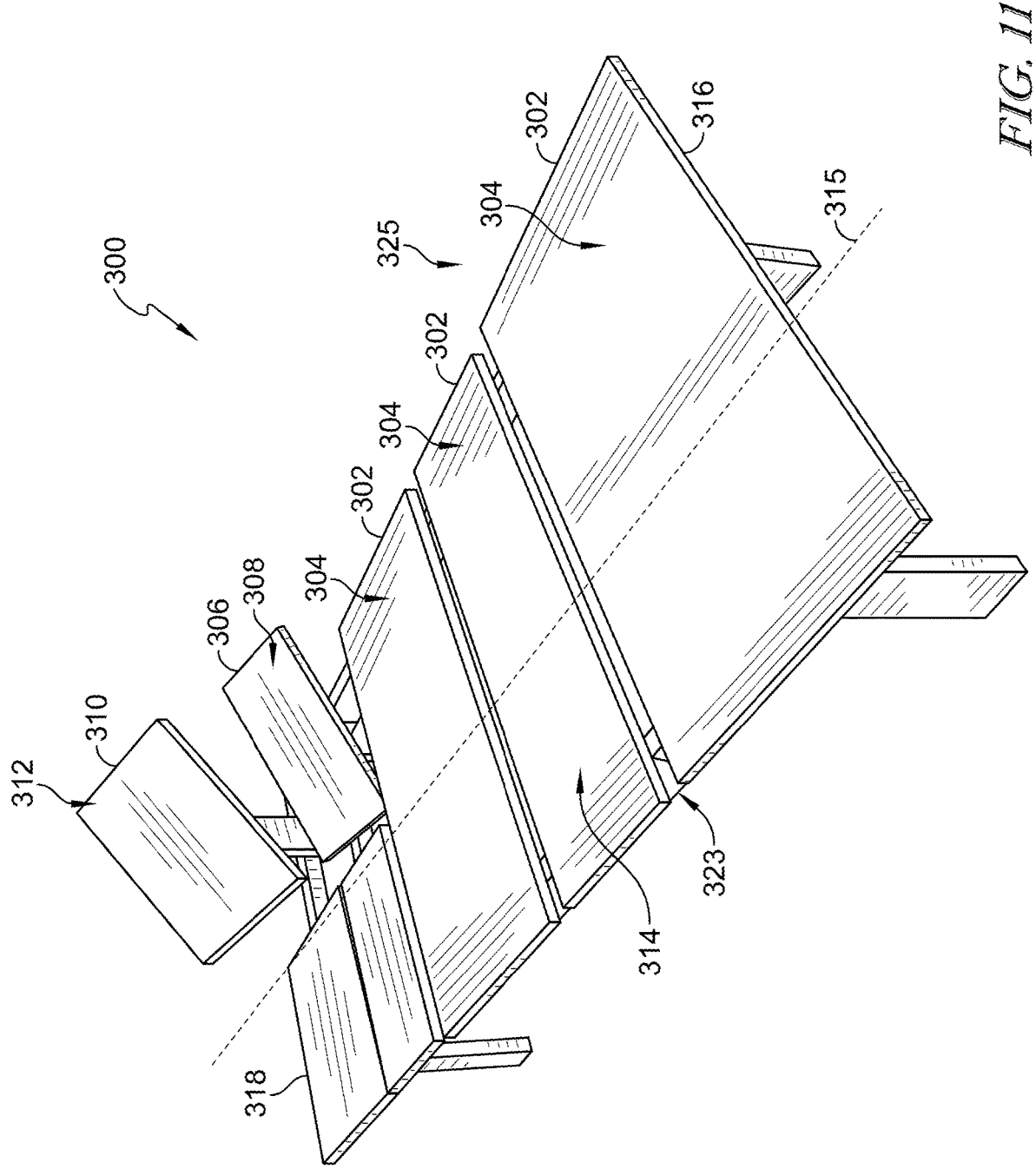
FIG. 11 is a perspective view of a lateral rotation apparatus in accordance with another embodiment.

Referring to FIG. 11 a lateral rotation apparatus 300 includes plurality of support sections, namely a plurality of leg support sections 302 forming a first support plane 304, a torso support section 306 forming a second support plane 308, and a head support section 310 forming a third support plane 312 that collectively define a multi-plane, sleep surface 314 that may be progressively angled along a longitudinal axis 315, from a first or bottom edge 316 of sleep surface 314 to an opposing second or top edge 318 of sleep surface 314, resulting in relatively greater rotation of the upper respiratory tract of the user (as necessary for efficacy in preventing obstructive apnea) and relatively lesser rotation in the lower body of the user (resulting in greater comfort and perceived stability by avoiding rotation of a majority of the user's body mass).

In one embodiment, the lateral rotation apparatus 300 supports a mattress. Each of the support sections 306 and 310 are coupled via linkage assemblies 320 (illustrated in FIG. 12) that enable support sections 306 and 310 to move relative to one another and relative to support section 302. For example, a first linkage assembly enables support section 306 to move relative to support section 302, and a second linkage assembly enables support section 310 to move relative to support section 306.

Figure 12:
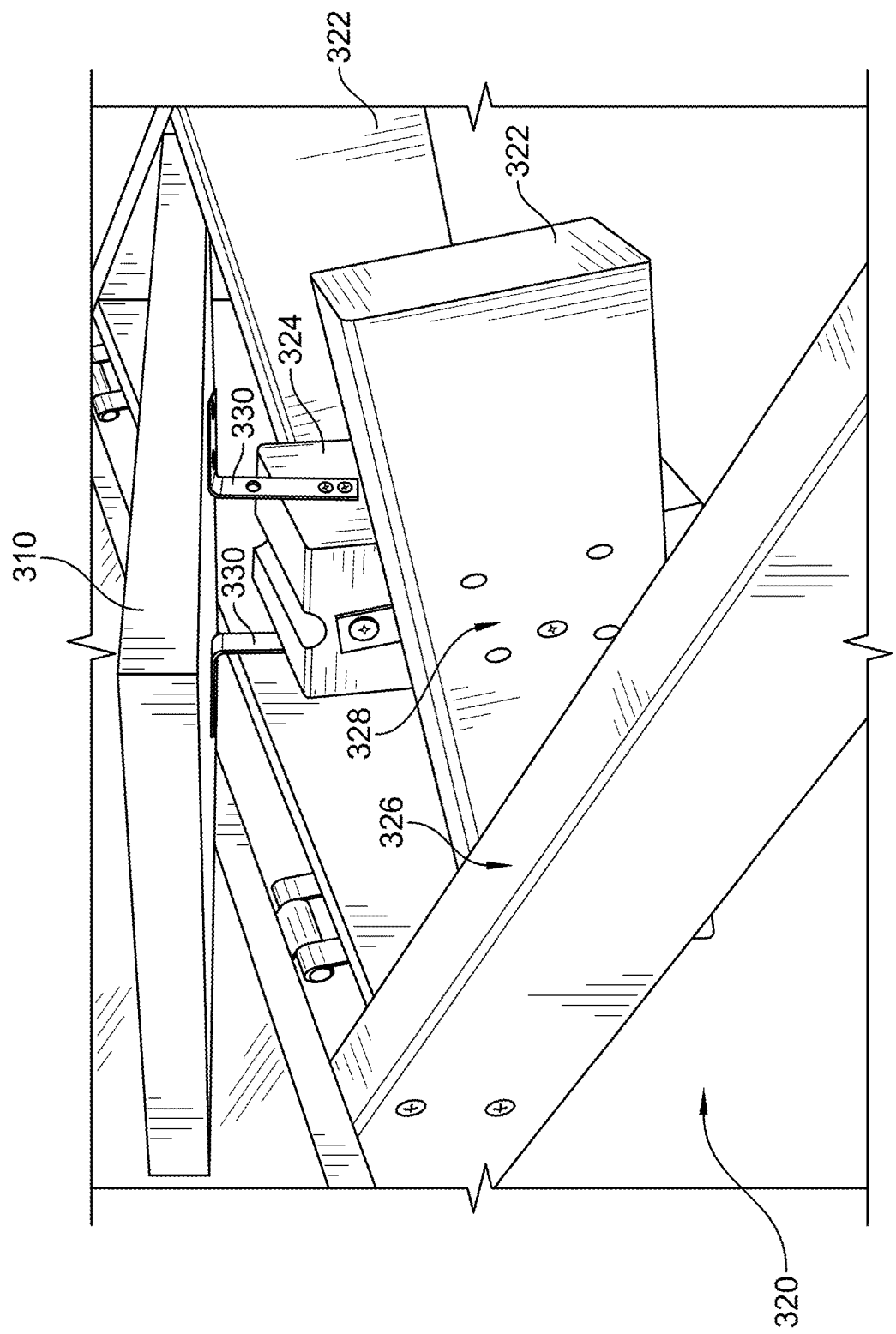
FIG. 12 is a perspective view of a linkage assembly of the lateral rotation apparatus of FIG. 11.

Referring to FIG. 12, a linkage assembly 320 for rotating the head section 310 is illustrated. Linkage assembly 320 includes a legs 322 extending substantially parallel to the longitudinal axis 315. In the illustrative embodiment, the assembly 320 includes a pair of legs 322 that are parallel to one another and rotate in unison. FIG. 12 illustrates a pair of legs 322 extending along a first side 323 (shown in FIG. 11) of the head section 310. In some embodiments, a second pair of legs 322 may extend along the second side 325 (shown in FIG. 11) of the head section 310. The leg 322 rotates relative to a plane that extends through the longitudinal axis 315 substantially parallel to the sleep surface 314 when the leg 322 is in a non-rotated position. That is, the leg 322 rotates about an axis 326 extending substantially perpendicular to the longitudinal axis 315 and substantially parallel to bottom edge 316 and top edge 318 of sleep surface 314. The leg 322 rotates to raise or lower one of the torso support section 306 or the head support section 310, as illustrated in FIG. 11. A first link 324 is coupled to the leg 322. In the illustrative embodiment, the first link 324 is coupled between the pair of legs 322. The first link 324 rotates with respect to the leg 322. Particularly, the first link 324 rotates about an axis 328 extending substantially parallel to bottom edge 316 and top edge 318 of sleep surface 314. At least one second link 330 couples the first link 324 and the head section 310. In the illustrated embodiment, a pair of second links 330 couple the first link 324 and the head section 310. The second link 330 rotates the head section 310 relative to the longitudinal axis 315. That is, the second link 330 rotates the head section 310 about an axis 332 that extends parallel to the longitudinal axis 315 so that the head section 310 is tilted to a head tilt angle.

In operation, the leg 322 is rotated about the axis 326 to a desired height. As the leg 322 is rotated upward, the first link 324 rotates about the axis 328 and the second link 330 rotates about the axis 332 such that the head section 310 is tilted relative to the longitudinal axis 315. Particularly, the head section 310 is tilted to a head stilt angle such that the first side 323 of the head section 310 is positioned above or higher than the second side 325 of the head section 310.

Also, the head section 310 is rotated so that a top edge 336 of the head section 310 is positioned above or higher than a bottom edge 338 of the head section 310. In some embodiments, only a leg 322 on the first side 323 of the head section 310 is rotated to achieve the desired head tilt angle. In some embodiments, the leg 322 on both the first side 323 and the second side 325 of the head section 310 are rotated.

It should be noted that the torso section 306 includes a linkage assembly that is substantially similar to the linkage assembly 320 and is operable to rotate the torso section 306 in the same manner to achieve a desired torso tilt angle. It should be appreciated that the lateral rotation apparatus 300 may be adjusted to achieve various angles. For example, the legs 322 may be adjusted to different angles to achieve the various head tilt angles and torso tilt angles described above. In one embodiment, a leg 322 may be operable to tilt at least one of the leg support sections 302 to an angle described above.

Figure 13:
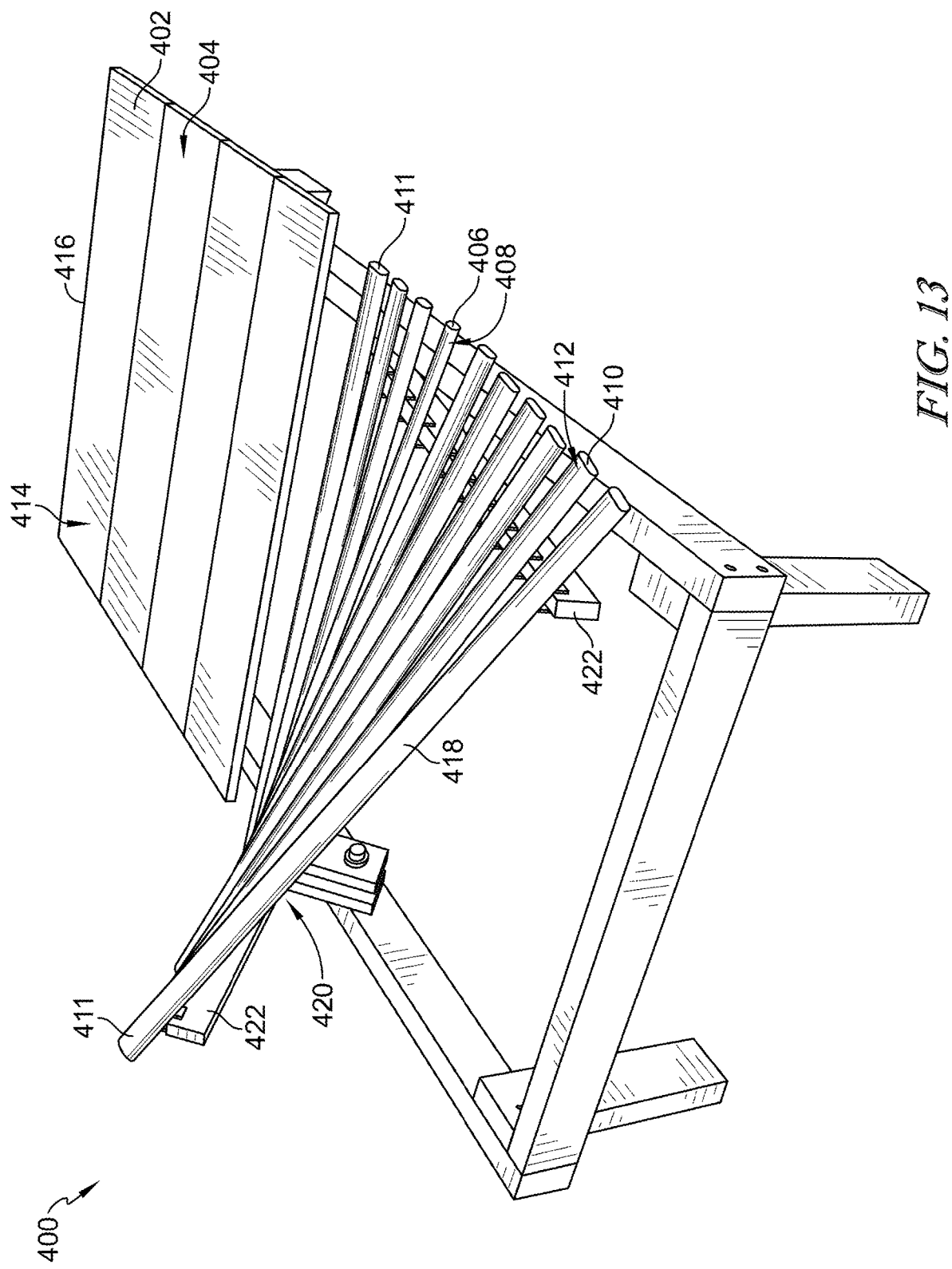
FIG. 13 is a perspective view of a lateral rotation apparatus in accordance with yet another embodiment.

Referring to FIG. 13, a lateral rotation apparatus 400 includes plurality of support sections, namely a leg support section 402 forming a first support plane 404, a torso support section 406 forming a second support plane 408, and a head support section 410 forming a third support plane 412 that collectively define a multi-plane, sleep surface 414 that may be progressively angled along a longitudinal axis 415, from a first or bottom edge 416 of sleep surface 414 to an opposing second or top edge 418 of sleep surface 414, resulting in relatively greater rotation of the upper respiratory tract of the user (as necessary for efficacy in preventing obstructive apnea) and relatively lesser rotation in the lower body of the user (resulting in greater comfort and perceived stability by avoiding rotation of a majority of the user's body mass).

In one embodiment, the lateral rotation apparatus 400 supports a mattress. Support sections 406 and 410 are comprised of a plurality of slats 411. Particularly, a first plurality of slats 413 forms the torso support section 406, and a second plurality of slats 417 forms the head support section 410. Each of the plurality of slats 411 is joined to a linkage assembly 420 (illustrated in FIG. 15) that enables support sections 406 and 410 to move relative to one another and relative to support section 402. In the illustrative embodiment, each of the support sections 406 and 410 is rotated is unison by the linkage assembly 420.

The linkage assembly 420 includes a pair of legs 422. A first leg 424 extends along a first side 426 of the lateral rotation apparatus 400 (and also the first side 426 of the torso support section 406 and the head support section 410). A second leg 428 extends along a second side 430 of the lateral rotation apparatus 400 (and also the second side 430 of the torso support section 406 and the head support section 410). The legs 422 rotate relative to a plane that extends through the longitudinal axis 315 substantially parallel to the sleep surface 414 when the leg 422 is in a non-rotated position. That is, the legs 422 rotate about an axis 426 extending substantially perpendicular to the longitudinal axis 415 and substantially parallel to bottom edge 416 and top edge 418 of sleep surface 414. The legs 422 rotate to raise or lower the torso support section 406 and the head support section 410. In some embodiments, both legs 422 are rotated to rotate the torso support section 406 and the head support section 410. In such an embodiment, the legs 422 may be rotated to different angles. Alternatively, the legs 422 may be rotated to the same angle. In some embodiments, only one of the legs 422 is rotated to rotate the torso support section 406 and the head support section 410.

Figure 14:
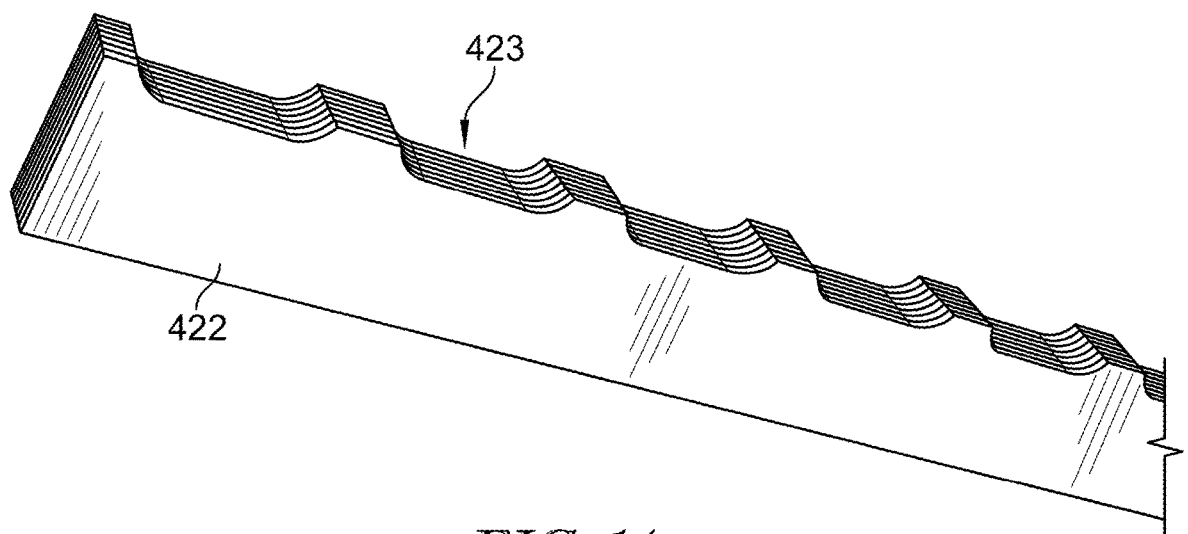
FIG. 14 is a perspective view of a leg of the lateral rotation apparatus of FIG. 13.
Figure 15:
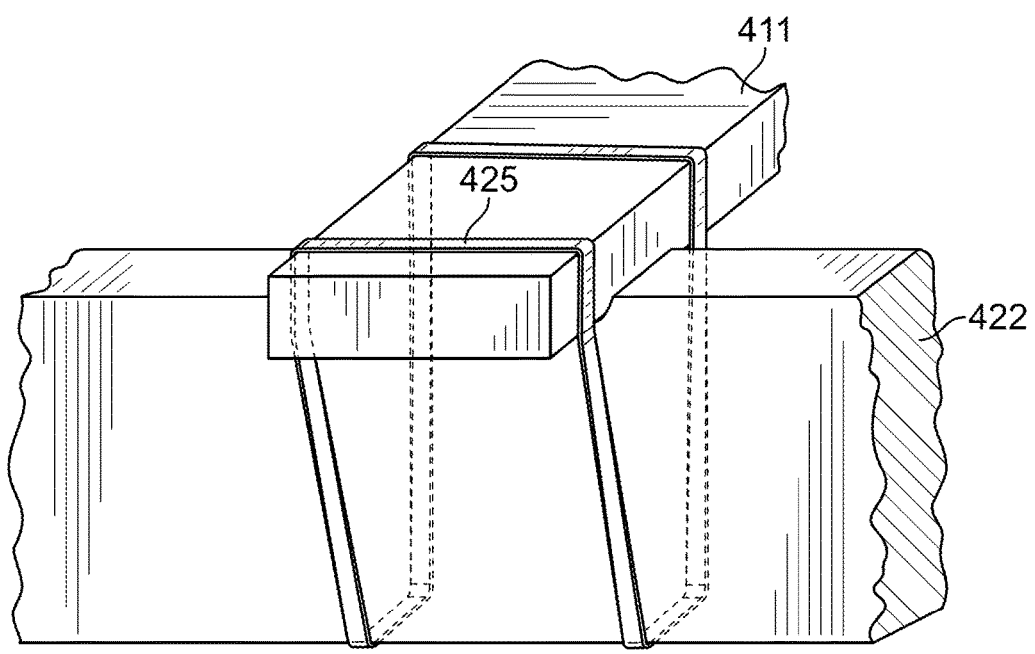
FIG. 15 is a perspective view of a linkage assembly of the lateral rotation apparatus of FIG. 13.

Referring to FIGS. 14 and 15, the legs 422 include notches 423 formed therein, wherein each notch 423 retains a slat 411. That is the notches 423 have a width that is substantially the same as a width of each slat 411. The slat 411 rests within the notch 423. In one embodiment, the slats 411 may have varying widths. For example, a slat 411 in support section 402 may have a width that is greater than a width of a slat 411 in support section 410, or vice versa. It should be noted that the support section 406 may also have slats 411 of a different width. In some embodiments, the slats 411 within any support section 402, 406, 410 may have varying widths. The notches 423 are sized to the width of the slat 411 that is positioned therein. The linkage assembly 420 shown in FIG. 15 includes an elastomeric material 425, for example a rubber band, that is wrapped around the slat 411 and the leg 422. The elastomeric material 425 enables the slat 411 to rotate within the notch 423, for example to a position illustrated in FIG. 13, while the slat 411 remains retained within the notch 423.

It should be appreciated that the lateral rotation apparatus 400 may be adjusted to achieve various angles. For example, the legs 422 may be adjusted to different angles to achieve the various head tilt angles and torso tilt angles described above. In one embodiment, the legs 422 may be operable to tilt the leg support section 402 to an angle described above.

Figure 16:
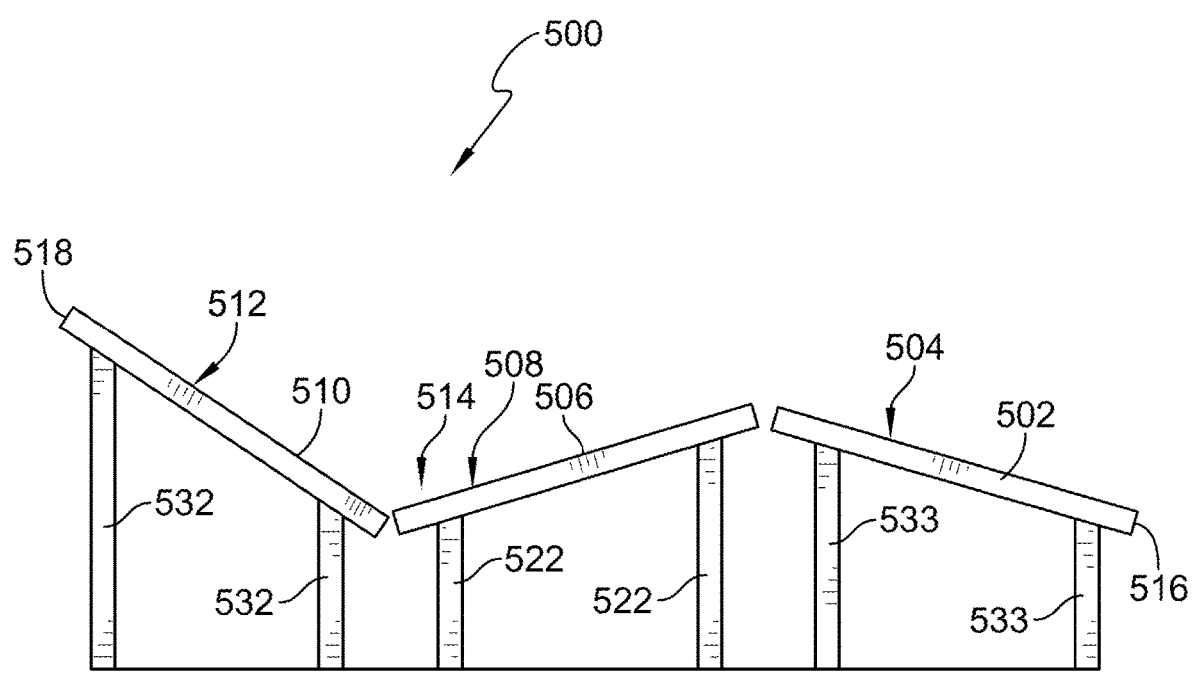
FIG. 16 is a perspective view of a lateral rotation apparatus in accordance with another embodiment and in a first position.
Figure 17:
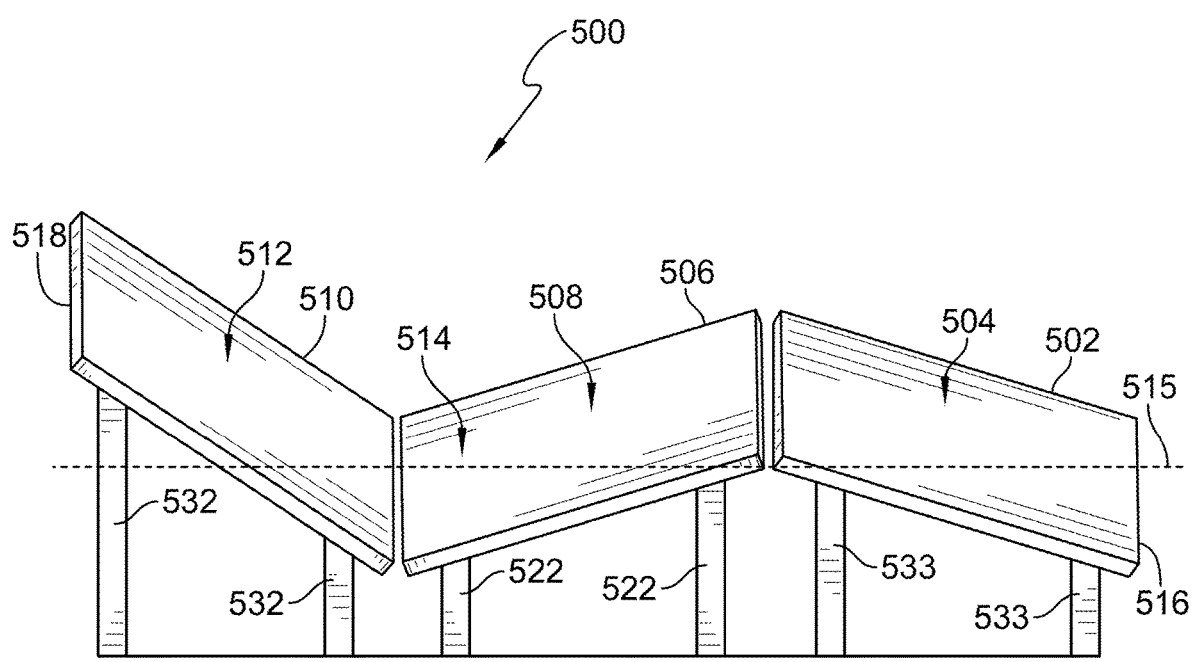
FIG. 17 is a perspective view of a lateral rotation apparatus in accordance with another embodiment and in a second position.

Referring to FIGS. 16 and 17, a lateral rotation apparatus 500 is embodied as a chair having plurality of support sections, namely a leg support section 502 forming a first support plane 504, a seating support section 506 forming a second support plane 508, and a torso/head support section 510 forming a third support plane 512 that collectively define a multi-plane, seating surface 514 that may be progressively angled along a centerline 515, from a first or bottom edge 516 of the apparatus 500 to an opposing second or top edge 518 of the apparatus 500, resulting in relatively greater rotation of the upper respiratory tract of the user (as necessary for efficacy in preventing obstructive apnea) and relatively lesser rotation in the lower body of the user (resulting in greater comfort and perceived stability by avoiding rotation of a majority of the user's body mass).

The apparatus 500 includes a first pair of legs 522. The legs 522 are adjustable in height to raise or lower the seating support section 506, as illustrated in FIG. 17. In some embodiments, both legs 522 are adjusted to rotate the seating support section 506. In such an embodiment, the legs 522 are adjusted to different heights. In some embodiments, only one of the legs 522 is adjusted to rotate the seating support section 506. A second pair of legs 532 extends along the head/torso support section 510. The legs 532 are adjustable in height to raise or lower the head/torso support section 510, as illustrated in FIG. 17. In some embodiments, both legs 532 are adjusted to rotate the head/torso support section 510. In such an embodiment, the legs 532 are adjusted to different heights. In some embodiments, only one of the legs 532 is adjusted to rotate the head/torso support section 510. A third pair of legs 533 extends along the leg support section 502. The legs 533 are adjustable in height to raise or lower the leg support section 502, as illustrated in FIG. 17. In some embodiments, both legs 533 are adjusted to rotate the leg support section 502. In such an embodiment, the legs 533 are adjusted to different heights. In some embodiments, only one of the legs 533 is adjusted to rotate the leg support section 502.

In some embodiments, a linkage assembly, such as the linkage assembly shown in FIG. 12 or FIG. 15, is utilized to rotate the seating support section 506 relative to the leg support section 402. A second linkage assembly, such as the linkage assembly shown in FIG. 12 or FIG. 15, is utilized to rotate the head/torso support section 410 relative to the seating support section 406. It should be appreciated that the lateral rotation apparatus 500 may be adjusted to achieve various angles. For example, the legs 522 and 532 may be adjusted to different angles to achieve the various head tilt angles and torso tilt angles described above. In one embodiment, the legs 522 and 532 may be operable to tilt the leg support section 502 to an angle described above.

It should be appreciated that any of the adjustable legs described above may be operable with an actuator, for example, a motor, a jack, a screw jack, a hydraulic cylinder, a crank, or the like.

Figure 18:
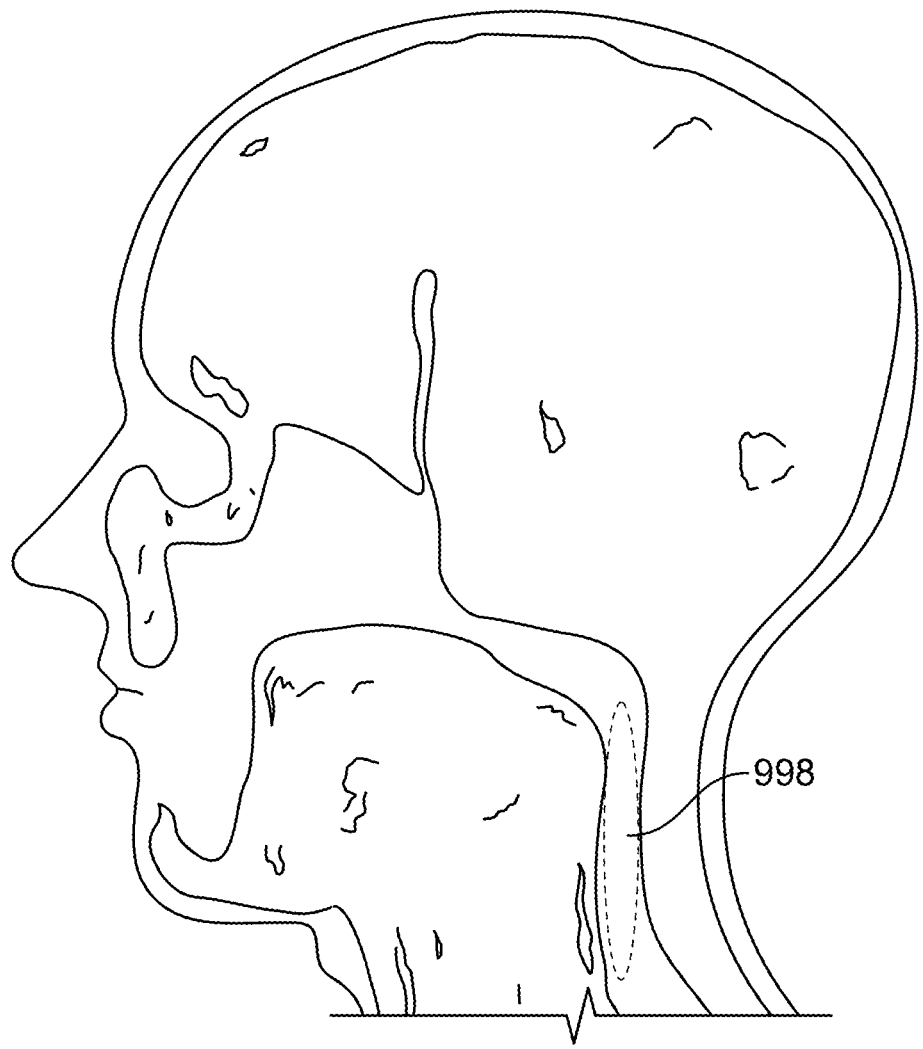
FIG. 18 is an MRI of a user laying on a support system in accordance with an embodiment.

Referring to FIG. 18, a sagittal distance 998 is defined in the airway of a user. The sagittal distance 998 is defined as an area of the user's esophagus that is opened while the user is laying on the support system 100. As illustrated in the graphs described below, the head tilt angle, the torso tilt angle and the leg tilt angle affects the sagittal distance 998 of the user.

Figure 19:
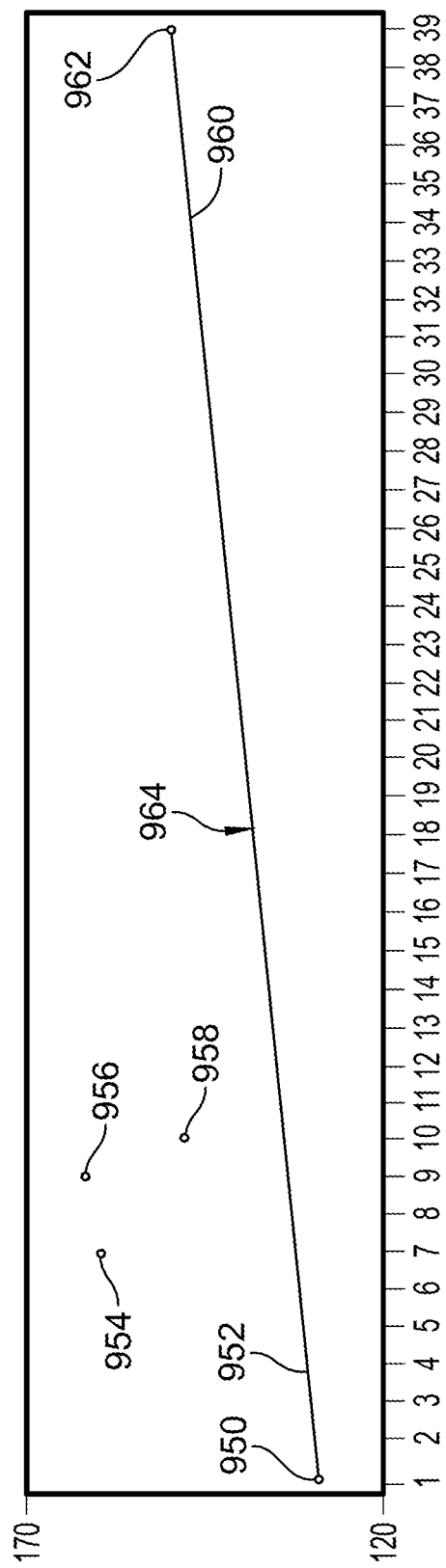
FIG. 19 is a graph is provided showing a minimum airway area in relation to various tilt angles.

Referring to FIG. 19, a graph is provided showing a minimum airway area in relation to various tilt angles. Based on prior research in the field of sleep medicine, it was believed that a subject with Positional Obstructive Sleep Apnea (POSA) will suffer a disproportionate number of Apnea—Hypopnea Index events (or number of airway obstructions) when in the supine position than in the non-supine positon (i.e., upper airway rotated 90 degrees away from vertical). It has been assumed that changes in the airway would be either linear as the upper airway is rotated from vertical to 90 degrees from vertical, or more likely that the relationship be more binary, and that changes in the upper airway would be primarily seen once the upper airway was rotated to at or about 90 degrees from vertical.

However, based on research using Magnetic Resonance Imaging of the upper airways of patient previously diagnosed with POSA, this was not the case. Rather, in relevant measurements of the upper airway (for example, measurement of the minimum airway area in the retroglossal region), the relationship between head/torso support and minimum airway area was neither linear nor binary between 0 degree and 90 degree positons. As illustrated in FIG. 19, the research found that minimum airway area increased much more rapidly than a linear relationship and reached that level of improvement far before the 90 degree positon.

From point 950 (head angle at 0 degrees, torso angle at 0 degrees), head angle increases by 2.5 degrees until it is 5 degrees greater than the torso angle, so at point 952 the head angle is at 5 degrees and the torso angle is at 0 degrees, after which the head and torso angles each increase by 2.5 degrees until the head degree reaches 90 degrees at point 960, after which the torso angle increases by 2.5 degrees until both the head and torso angles are at 90 degrees at point 962. In FIG. 19, minimum airway area is plotted at point 950 (head angle at 0 degrees, torso angle at 0 degrees), point 954 (head angle at 15 degrees, torso angle at 10 degrees), point 956 (head angle at 20 degrees, torso angle at 15 degrees), point 958 (head angle at 22.5 degrees, torso angle at 17.5 degrees) and point 962 (head angle at 90 degrees, torso angle at 90 degrees), with the linear extrapolation between the measurements at point 950 and point 962 shown as line 964.

Referring to FIGS. 20-23, specific examples of measured sagittal distances 998 are represented through a series of graphs. It should be noted that the examples and data represented in the graphs of FIGS. 20-23 are exemplary only and non-limiting. It will be appreciated that various studies may be provided that result in other examples of data.

Figure 20:
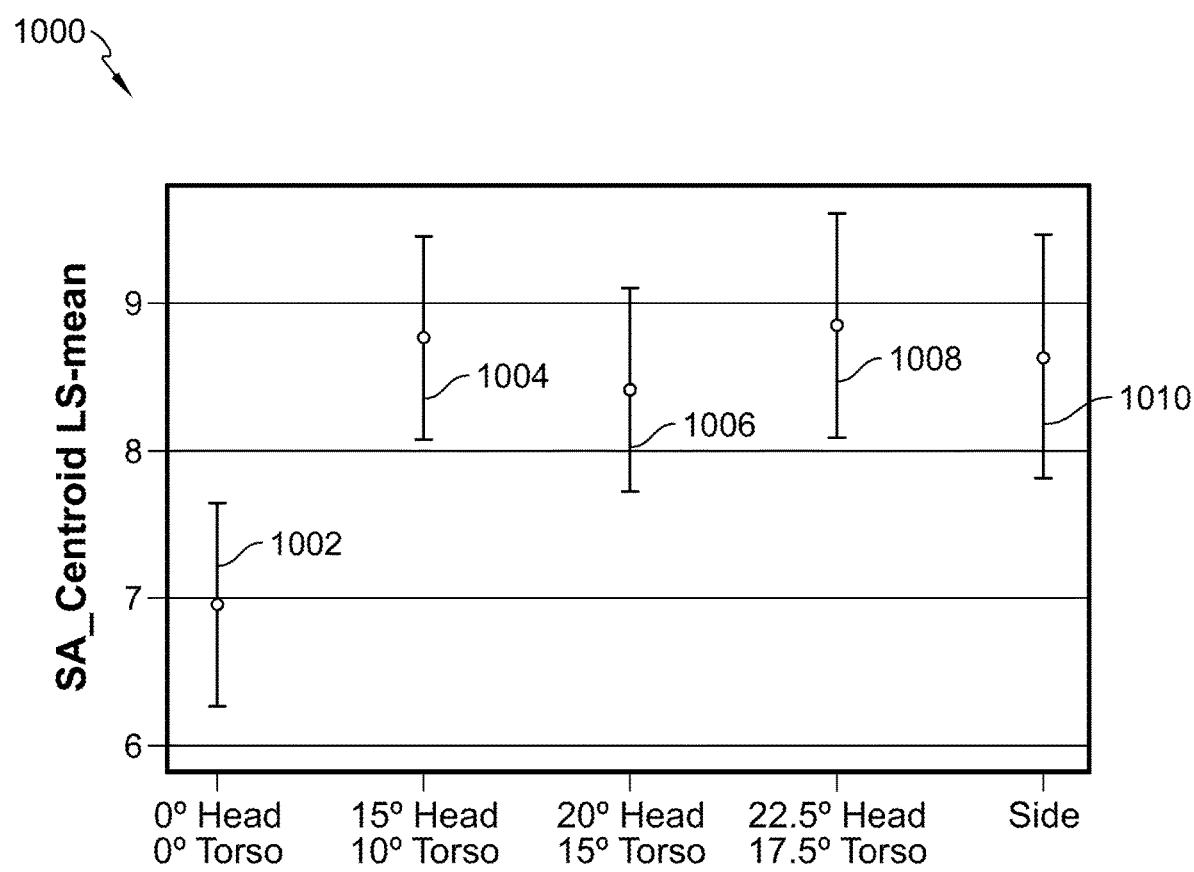
FIG. 20 is a graph of sleep surface orientations versus a minimum sagittal distance taken in a retroglossal region of a user positioned on the sleep surface.

Referring to FIG. 20, the graph 1000 illustrates sleep orientations on the x-axis versus a minimum sagittal distance on the y-axis in the retroglossal region of a user positioned on the sleep surface 114. As illustrated by line 1002, the minimum sagittal distance for a user in the supine position with the head at 0° with respect to the horizontal support plane 124 and the torso at 0° with respect to the horizontal support plane 124 is between approximately 6.25 $mm^2$ and approximately 7.75 $mm^2$ with a mean minimum sagittal distance of approximately 7 $mm^2$. As illustrated by line 1004, the minimum sagittal distance for a user with the lateral rotation apparatus rotating the head at 15° with respect to the horizontal support plane 124 and rotating the torso at 10° with respect to the horizontal support plane 124 is between approximately 8 $mm^2$ and approximately 9.5 $mm^2$ with a mean minimum sagittal distance of approximately 8.75 $mm^2$. As illustrated by line 1006, the minimum sagittal distance for a user with the lateral rotation apparatus rotating the head at 20° with respect to the horizontal support plane 124 and rotating the torso at 15° with respect to the horizontal support plane 124 is between approximately 7.75 $mm^2$ and approximately 9 $mm^2$ with a mean minimum sagittal distance of approximately 8.5 $mm^2$. As illustrated by line 1008, the minimum sagittal distance for a user with the lateral rotation apparatus rotating the head at 22.5° with respect to the horizontal support plane 124 and rotating the torso at 17.5° with respect to the horizontal support plane 124 is between approximately 8 $mm^2$ and approximately 9.75 $mm^2$ with a mean minimum sagittal distance of approximately 8.75 $mm^2$. As illustrated by line 1010, the minimum sagittal distance for a user lying on their side is between approximately 7.75 $mm^2$ and approximately 9.5 $mm^2$ with a mean minimum sagittal distance of approximately 8.5 $mm^2$. Accordingly, the user of the sleep surface 114 has a greater minimum sagittal distance when lying with the head at 22.5° with respect to the horizontal support plane 124 and rotating the torso at 17.5° with respect to the horizontal support plane 124 or when lying with the head at 15° with respect to the horizontal support plane 124 and rotating the torso at 10° with respect to the horizontal support plane 124. In all positions on the lateral rotation apparatus 200, the user has a greater minimum sagittal distance when compared to lying supine.

Figure 21:
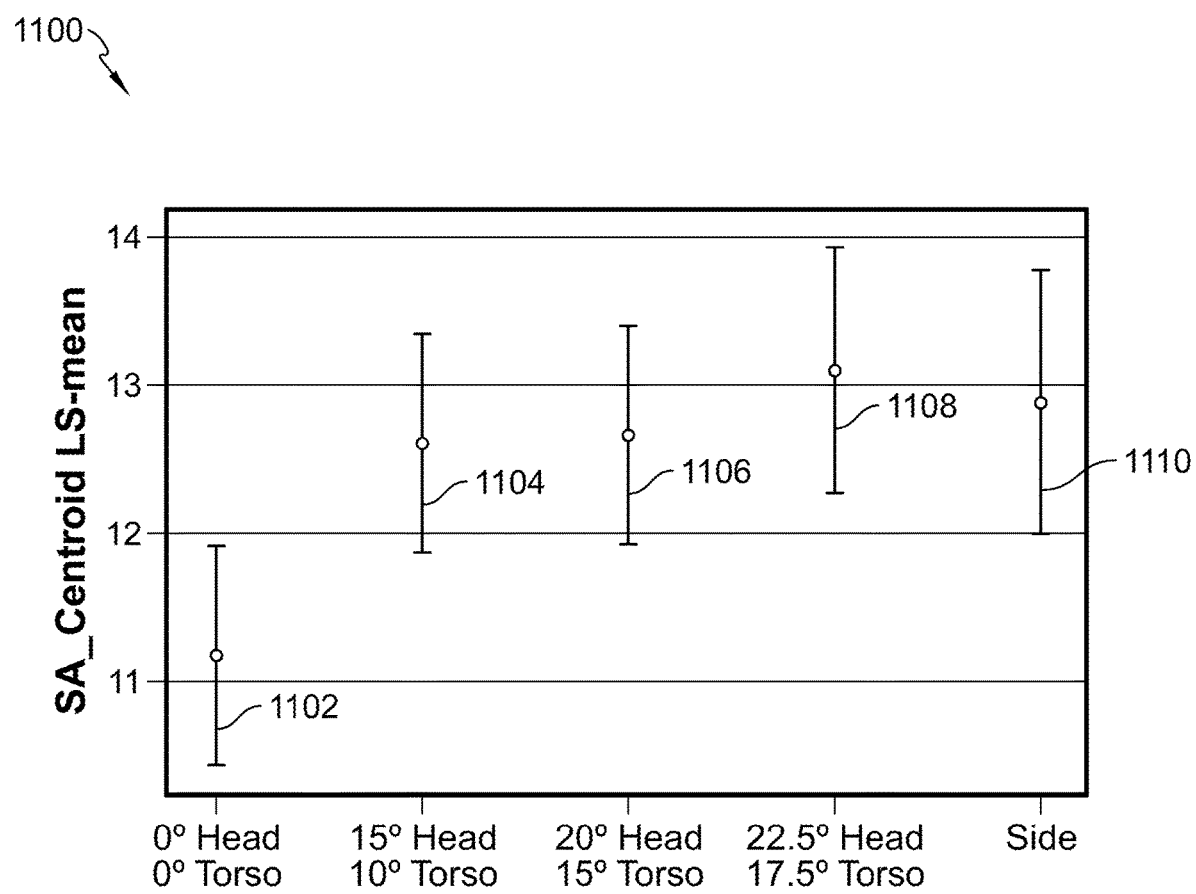
FIG. 21 is a graph of sleep surface orientations versus an average sagittal distance taken in a retroglossal region of a user positioned on the sleep surface.

Referring to FIG. 21, the graph 1100 illustrates sleep orientations on the x-axis versus an average sagittal distance on the y-axis taken in a retroglossal region of a user positioned on the sleep surface 114. As illustrated by line 1102, the average sagittal distance for a user in the supine position with the head at 0° with respect to the horizontal support plane 124 and the torso at 0° with respect to the horizontal support plane 124 is between approximately 10.25 $mm^2$ and approximately 11.75 $mm^2$ with a mean average sagittal distance of approximately 11.25 $mm^2$. As illustrated by line 1104, the average sagittal distance for a user with the lateral rotation apparatus rotating the head at 15° with respect to the horizontal support plane 124 and rotating the torso at 10° with respect to the horizontal support plane 124 is between approximately 11.75 $mm^2$ and approximately 13.5 with a mean average sagittal distance of approximately 12.5 $mm^2$. As illustrated by line 1006, the average sagittal distance for a user with the lateral rotation apparatus rotating the head at 20° with respect to the horizontal support plane 124 and rotating the torso at 15° with respect to the horizontal support plane 124 is between approximately 11.75 $mm^2$ and approximately 13.5 $mm^2$ with a mean average sagittal distance of approximately 12.5 $mm^2$. As illustrated by line 1008, the average sagittal distance for a user with the lateral rotation apparatus rotating the head at 22.5° with respect to the horizontal support plane 124 and rotating the torso at 17.5° with respect to the horizontal support plane 124 is between approximately 12.25 mm$^2$ and approximately 13.75 mm$^2$ with a mean average sagittal distance of approximately 13.25 mm$^2$. As illustrated by line 1110, the average sagittal distance for a user lying on their side is between approximately 12 and approximately 13.75 mm$^2$ with a mean average sagittal distance of approximately 12.75 mm$^2$. Accordingly, the user of the sleep surface 114 has a greater average sagittal distance when lying with the head at 22.5° with respect to the horizontal support plane 124 and rotating the torso at 17.5° with respect to the horizontal support plane 124. In all positions on the lateral rotation apparatus 200, the user has a greater average sagittal distance when compared to lying supine.

Figure 22:
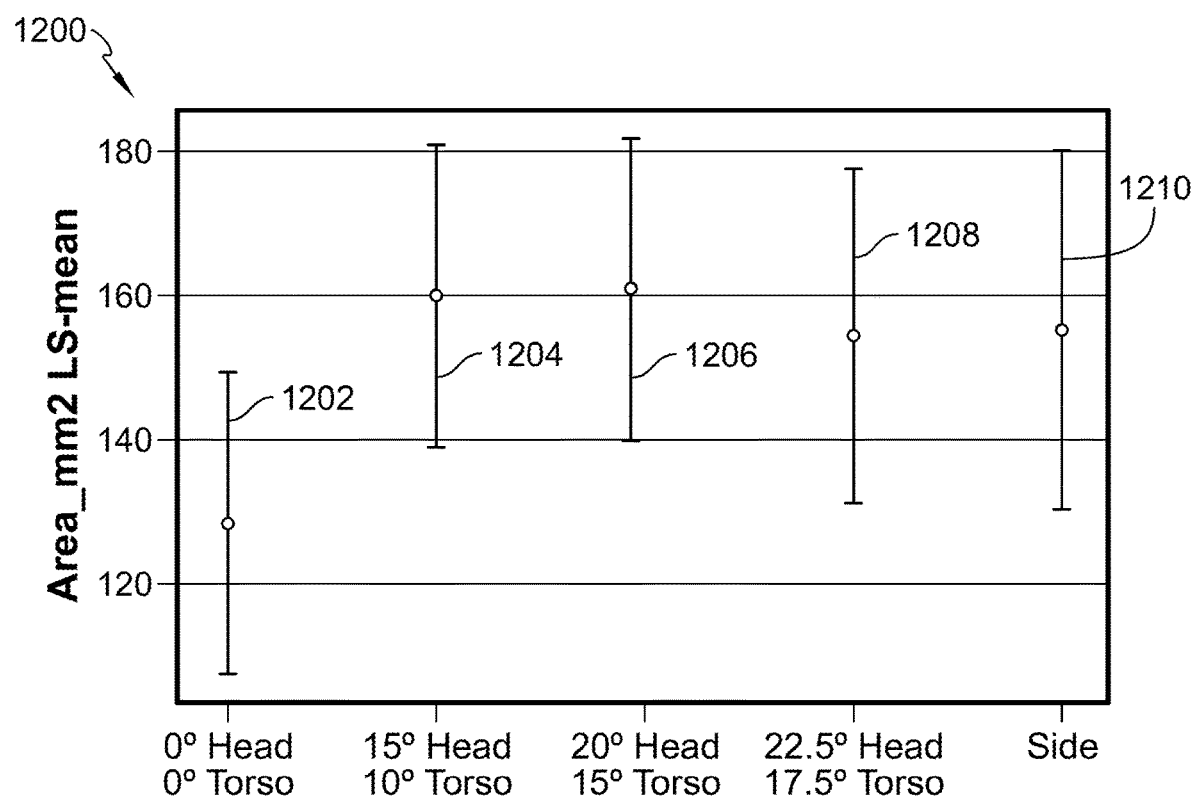
FIG. 22 is a graph of sleep surface orientations versus a minimum airway area taken in a retroglossal region of a user positioned on the sleep surface.

Referring to FIG. 22, the graph 1200 illustrates sleep orientations on the x-axis versus a minimum airway area on the y-axis taken in the retroglossal region of a user positioned on the sleep surface 114. As illustrated by line 1202, the minimum airway area in the retroglossal region for a user in the supine position with the head at 0° with respect to the horizontal support plane 124 and the torso at 0° with respect to the horizontal support plane 124 is between approximately 105 mm$^2$ and approximately 150 mm$^2$ with a mean minimum airway area in the retroglossal region of approximately 130. As illustrated by line 1204, the minimum airway area in the retroglossal region for a user with the lateral rotation apparatus rotating the head at 15° with respect to the horizontal support plane 124 and rotating the torso at 10° with respect to the horizontal support plane 124 is between approximately 140 mm$^2$ and approximately 180 mm$^2$ with a mean minimum airway area in the retroglossal region of approximately 160 mm$^2$. As illustrated by line 1206, the minimum airway area in the retroglossal region for a user with the lateral rotation apparatus rotating the head at 20° with respect to the horizontal support plane 124 and rotating the torso at 15° with respect to the horizontal support plane 124 is between approximately 140 mm$^2$ and approximately 185 mm$^2$ with a mean minimum airway area in the retroglossal region of approximately 185 mm$^2$. As illustrated by line 1208, the minimum airway area in the retroglossal region for a user with the lateral rotation apparatus rotating the head at 22.5° with respect to the horizontal support plane 124 and rotating the torso at 17.5° with respect to the horizontal support plane 124 is between approximately 130 mm$^2$ and approximately 175 mm$^2$ with a mean minimum airway area in the retroglossal region of approximately 155 mm$^2$. As illustrated by line 1210, the minimum airway area in the retroglossal region for a user lying on their side is between approximately 130 mm$^2$ and approximately 180 mm$^2$ with a mean minimum airway area in the retroglossal region of approximately 155 mm$^2$. In all positions on the lateral rotation apparatus 200, the user has a greater average sagittal distance when compared to lying supine. For example, the user of the sleep surface 114 has a 24.6% greater mean minimum airway area than lying supine when lying with the head at 15° with respect to the horizontal support plane 124 and the torso at 10° with respect to the horizontal support plane 124 or when lying with the head at 20° with respect to the horizontal support plane 124 and the torso at 15° with respect to the horizontal support plane 124.

Figure 23:
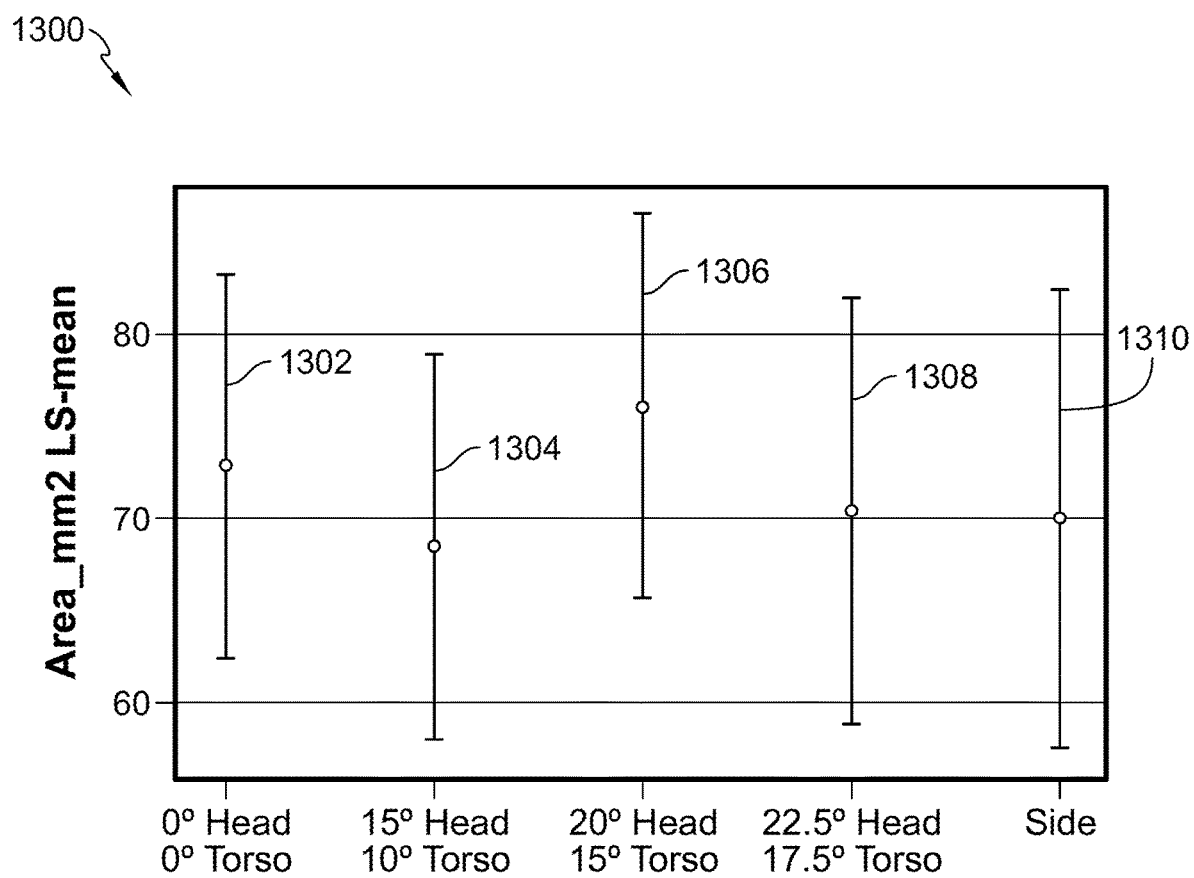
FIG. 23 is a graph of sleep surface orientations versus a minimum airway area taken in a retropalatal region of a user positioned on the sleep surface.

Referring to FIG. 23, the graph 1300 illustrates sleep orientations on the x-axis versus a minimum airway area on the y-axis taken in the retropalatal region of a user positioned on the sleep surface 114. As illustrated by line 1302, the minimum airway area in the retropalatal region for a user in the supine position with the head at 0° with respect to the horizontal support plane 124 and the torso at 0° with respect to the horizontal support plane 124 is between approximately 62.5 mm$^2$ and approximately 85 mm$^2$ with a mean minimum airway area in the retropalatal region of approximately 72.5 mm$^2$. As illustrated by line 1304, the minimum airway area in the retropalatal region for a user with the lateral rotation apparatus rotating the head at 15° with respect to the horizontal support plane 124 and rotating the torso at 10° with respect to the horizontal support plane 124 is between approximately 57.5 mm$^2$ and approximately 77.5 mm$^2$ with a mean minimum airway area in the retropalatal region of approximately 67.5 mm$^2$. As illustrated by line 1306, the minimum airway area in the retropalatal region for a user with the lateral rotation apparatus rotating the head at 20° with respect to the horizontal support plane 124 and rotating the torso at 15° with respect to the horizontal support plane 124 is between approximately 65 mm$^2$ and approximately 87.5 mm$^2$ with a mean minimum airway area in the retropalatal region of approximately 75 mm$^2$. As illustrated by line 1308, the minimum airway area in the retropalatal region for a user with the lateral rotation apparatus rotating the head at 22.5° with respect to the horizontal support plane 124 and rotating the torso at 17.5° with respect to the horizontal support plane 124 is between approximately 57.5 mm$^2$ and approximately 82.5 mm$^2$ with a mean minimum airway area in the retropalatal region of approximately 70 mm$^2$. As illustrated by line 1310, the minimum airway area for a user lying on their side is between approximately 55 mm$^2$ and approximately 82.5 mm$^2$ with a mean minimum airway area in the retropalatal region of approximately 70 mm$^2$. The user of the sleep surface 114 has a greater mean minimum airway area in the retropalatal region than lying supine when lying with the head at 20° with respect to the horizontal support plane 124 and the torso at 15° with respect to the horizontal support plane 124.

Figure 24A:
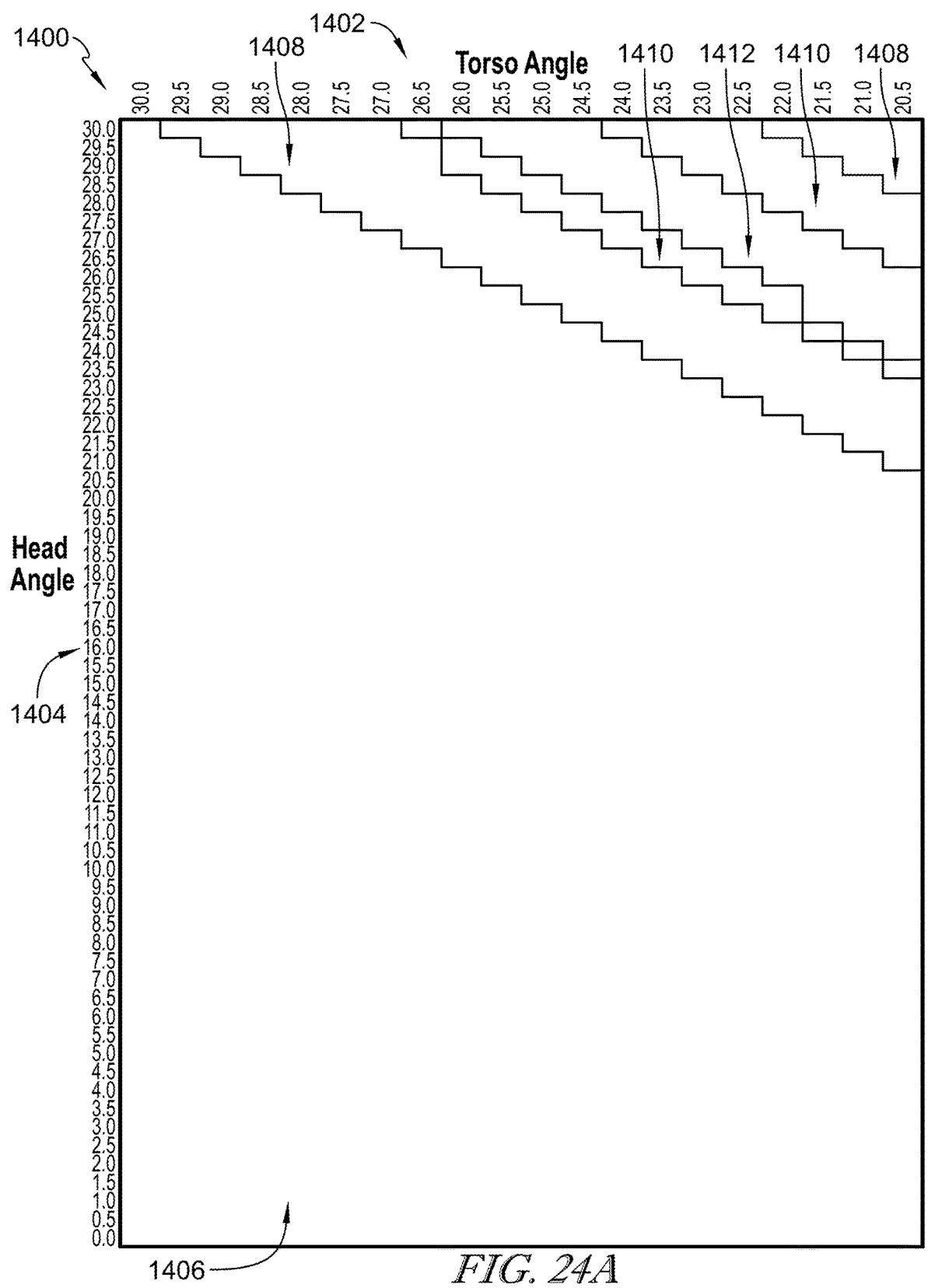
FIGS. 24A-24C illustrate an exemplary matrix of torso angles versus head angles that may be used to improve POSA and reduce the number of Apnea—Hypopnea Index events.
Figure 24B:
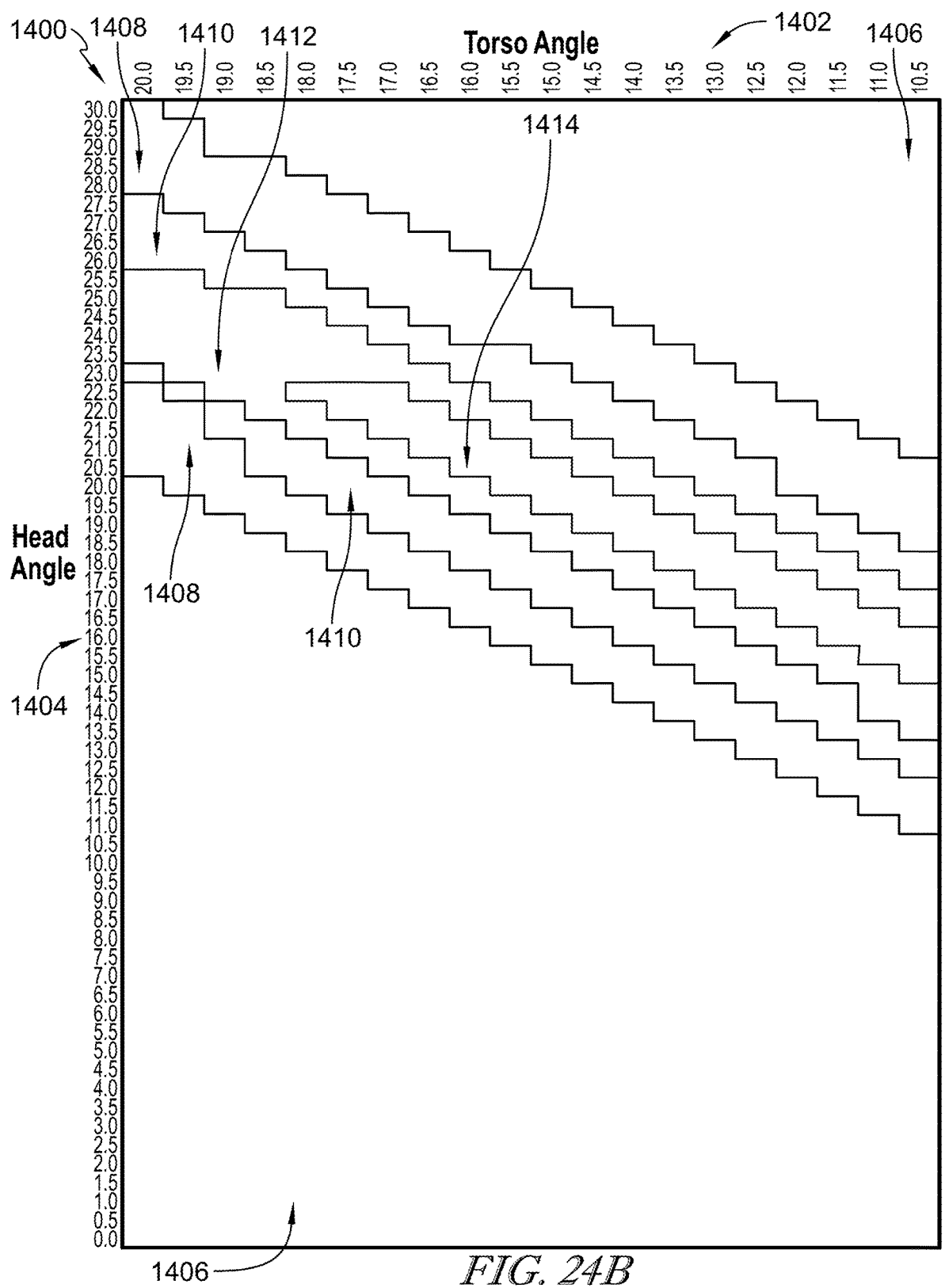
Figure 24C:
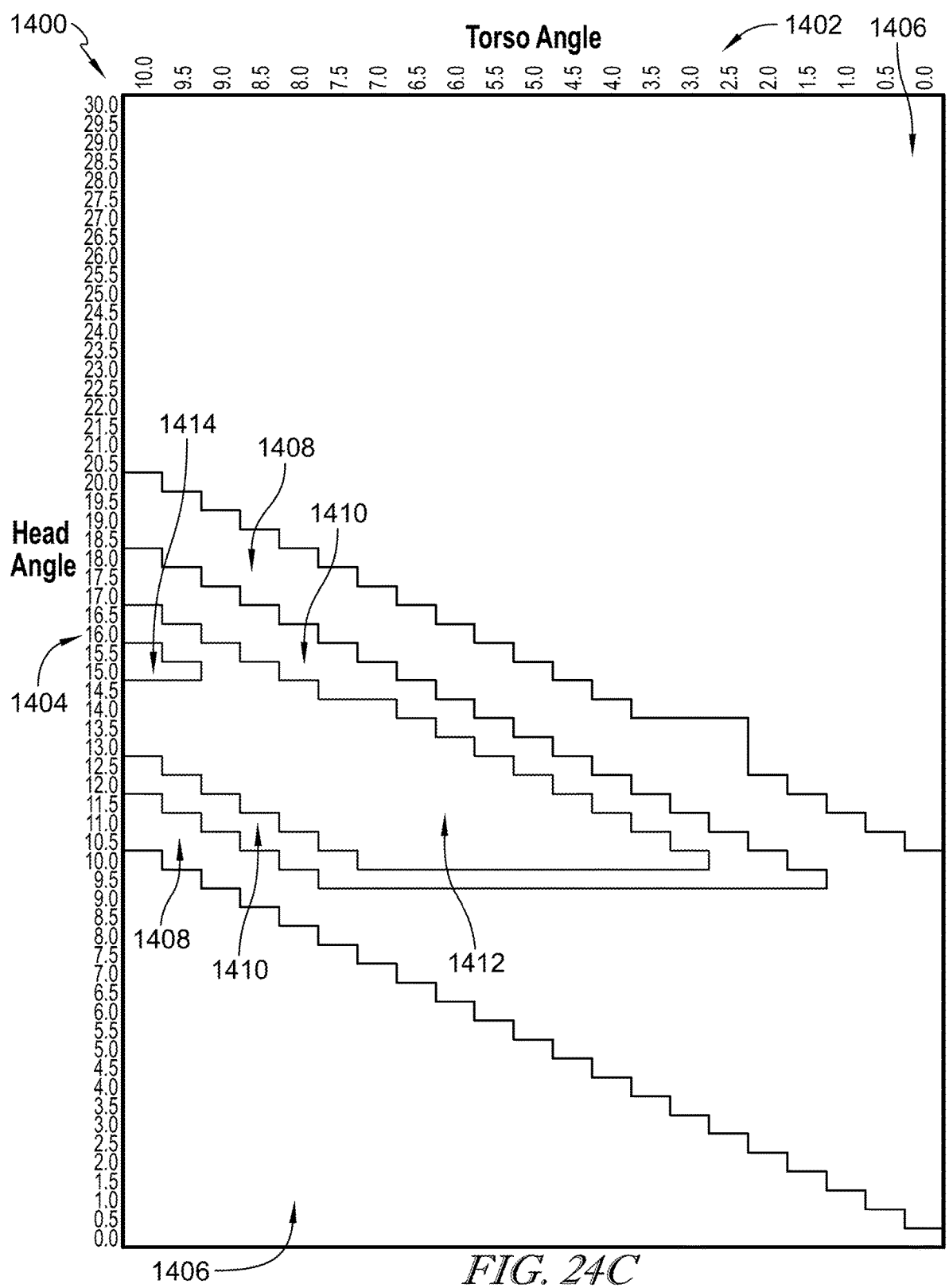

FIGS. 24A-24C illustrate an exemplary matrix 1400 of torso angles 1402 versus head angles 1404 that may be used to improve POSA and reduce the number of Apnea—Hypopnea Index events. The area 1406 illustrates combinations of torso angles 1402 and head angles 1404 that are generally considered unacceptable for improving POSA and reducing the number of Apnea—Hypopnea Index events. The area 1408 illustrates combinations of torso angles 1402 and head angles 1404 that are generally considered suboptimal for improving POSA and reducing the number of Apnea—Hypopnea Index events. The area 1410 illustrates combinations of torso angles 1402 and head angles 1404 that are generally considered good or fair for improving POSA and reducing the number of Apnea—Hypopnea Index events. The area 1412 illustrates combinations of torso angles 1402 and head angles 1404 that are generally considered very good for improving POSA and reducing the number of Apnea—Hypopnea Index events. The area 1414 illustrates combinations of torso angles 1402 and head angles 1404 that are generally considered excellent for improving POSA and reducing the number of Apnea—Hypopnea Index events.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

The invention claimed is:

1. A lateral rotation apparatus, comprising:
   a person support surface comprising head, torso and leg segments each having an independently rotatable person support plane;
   a first pair of adjustable legs positioned directly on a floor below a first end of the head segment, the first pair of adjustable legs comprising a first leg and a second leg, at least one of the first leg and the second leg of the first pair of adjustable legs being adjustable such that a height of the first leg is greater than a height of the second leg to rotate the head segment to a head tilt angle approximately at a centerline of the head segment in the range of about 7 to about 30 degrees relative to a horizontal support plane;
   a second pair of adjustable legs positioned directly on the floor below a second end of the head segment, the second pair of adjustable legs comprising a first leg and a second leg, at least one of the first leg and the second leg of the first pair of adjustable legs being adjustable to a height greater than a height of each of the first leg and second leg of the second pair of adjustable legs, and
   a third pair of adjustable legs positioned directly on the floor below the torso segment, the third pair of adjustable legs comprising a first leg and a second leg, at least one of the first leg and the second leg of the third pair of adjustable legs being adjustable such that a height of the first leg is greater than a height of the second leg to rotate the torso segment to a torso tilt angle approximately at a centerline of the torso segment that is within a range of about 5 degrees to about 10 degrees less than the head tilt angle,
   wherein the first pair of adjustable legs, the second pair of adjustable legs and the third pair of adjustable legs provide a graduated lateral rotation of the person support surface.

2. The lateral rotation apparatus of claim 1, wherein the first leg of the first pair of adjustable legs positions a first side of the head segment at a height greater than a second side of the head segment.

3. The lateral rotation apparatus of claim 1, wherein the first leg of the third pair of adjustable legs positions a first side of the torso segment at a height greater than a second side of the torso segment.

4. The lateral rotation apparatus of claim 1, wherein at least one of the first leg or the second leg of the first pair of adjustable legs comprises a telescoping leg.

5. The lateral rotation apparatus of claim 1, wherein at least one of the first leg or the second leg of the third pair of adjustable legs comprises a telescoping leg.

6. The lateral rotation apparatus of claim 1, wherein a height of at least one of the first leg or the second leg of the first pair of adjustable legs is adjusted with an actuator.

7. The lateral rotation apparatus of claim 6, wherein the actuator further comprises an electromechanical device configured to drive a height adjustment of the at least one of the first leg or the second leg of the first pair of adjustable legs.

8. The lateral rotation apparatus of claim 1, wherein a height of at least one of the first leg or the second leg of the third pair of adjustable legs is adjusted with an actuator.

9. The lateral rotation apparatus of claim 8, wherein the actuator further comprises an electromechanical device configured to drive a height adjustment of the at least one of the first leg or the second leg of the third pair of adjustable legs.

10. The lateral rotation apparatus of claim 1, wherein the head segment is coupled to the torso segment via a linkage assembly that enables rotation of the head segment with respect to the torso segment.

11. The lateral rotation apparatus of claim 1, wherein the torso segment is coupled to the leg segment via a linkage assembly that enables rotation of the torso segment with respect to the leg segment.

12. The lateral rotation apparatus of claim 1, wherein the torso segment is rotated to a torso tilt angle approximately at a centerline of the torso segment in the range of about zero to about 25 degrees.

13. The lateral rotation apparatus of claim 1, wherein the head segment is rotated to a head tilt angle approximately at a centerline of the head segment in the range of about 10 to about 15 degrees.

14. The lateral rotation apparatus of claim 13, wherein the torso segment is rotated to a torso tilt angle approximately at a centerline of the torso segment in the range of about 5 to about 10 degrees.

15. The lateral rotation apparatus of claim 1, further comprising a fourth pair of adjustable legs positioned under the leg segment and operable to rotate the leg segment to a leg tilt angle approximately at a centerline of the leg segment in the range of about 0 to about 5 degrees.

16. The lateral rotation apparatus of claim 1, wherein a height of at least one of the first leg or the second leg of the first pair of adjustable legs is linearly adjustable.

17. The lateral rotation apparatus of claim 1, wherein a height of at least one of the first leg or the second leg of the second pair of adjustable legs is linearly adjustable.

18. The lateral rotation apparatus of claim 1, wherein a height of at least one of the first leg or the second leg of the third pair of adjustable legs is linearly adjustable.

19. The lateral rotation apparatus of claim 15, wherein a height of the fourth pair of adjustable legs is linearly adjustable.

* * * * *